US010165959B2

(12) United States Patent
Colbaugh et al.

(10) Patent No.: US 10,165,959 B2
(45) Date of Patent: Jan. 1, 2019

(54) METHOD AND APPARATUS FOR DIAGNOSING OBSTRUCTIVE SLEEP APNEA WITH AN AWAKE PATIENT

(75) Inventors: Michael Edward Colbaugh, Level Green, PA (US); Ronald Dean Dean Fligge, Greensburg, PA (US); Vijay Kumar Iyer, Export, PA (US); Douglas Mechlenburg, Murrysville, PA (US); Edmund Arnliot Shaw, Pittsburgh, PA (US); Nathan Zimmerman, Murrysville, PA (US)

(73) Assignee: Koninklijke Philips N.V., Eindhoven (NL)

(*) Notice: Subject to any disclaimer, the term of this patent is extended or adjusted under 35 U.S.C. 154(b) by 478 days.

(21) Appl. No.: 13/878,591

(22) PCT Filed: Oct. 12, 2011

(86) PCT No.: PCT/IB2011/054504
§ 371 (c)(1),
(2), (4) Date: Jul. 1, 2013

(87) PCT Pub. No.: WO2012/052882
PCT Pub. Date: Apr. 26, 2012

(65) Prior Publication Data
US 2013/0289401 A1 Oct. 31, 2013

Related U.S. Application Data

(60) Provisional application No. 61/394,862, filed on Oct. 20, 2010, provisional application No. 61/442,447, filed on Feb. 14, 2011.

(51) Int. Cl.
*A61B 5/0488* (2006.01)
*A61B 5/00* (2006.01)
(Continued)

(52) U.S. Cl.
CPC .......... *A61B 5/0488* (2013.01); *A61B 5/4818* (2013.01); *A61B 7/003* (2013.01); *A61B 8/08* (2013.01)

(58) Field of Classification Search
None
See application file for complete search history.

(56) References Cited

U.S. PATENT DOCUMENTS

| 6,048,322 A | 4/2000 | Kushida | |
| 6,062,216 A * | 5/2000 | Corn | A61B 5/113 128/204.23 |

(Continued)

FOREIGN PATENT DOCUMENTS

| CN | 101238982 A | 8/2008 |
| JP | 2005003366 A | 1/2005 |

(Continued)

OTHER PUBLICATIONS

"Spectral Analysis of Activity of Laryngeal and Orofacial Muscles in Stutterers", Journal of Neurology, 1993, vol. 56, 1303-1311.*

(Continued)

Primary Examiner — Katherine Fernandez
Assistant Examiner — Marjan Saboktakin

(57) ABSTRACT

An apparatus for use in diagnosing the presence of obstructive sleep apnea (OSA) in a patient includes a sensing module structured to measure a parameter indicative of a tremor in the patient's neck, tongue and/or throat muscles while the patient is awake, the parameter not being airflow through the patient's airway. The sensing module generates one or more electrical signals based on the measured parameter. The apparatus also includes a processor operatively coupled to the sensing module, the processor being structured to receive the one or more electrical signals, perform an analysis of the one or more electrical signals, and based on the analysis determine whether the tremor has a fre- (Continued)

quency in at least one predetermined frequency range that is indicative of OSA.

21 Claims, 10 Drawing Sheets

(51) Int. Cl.
*A61B 7/00* (2006.01)
*A61B 8/08* (2006.01)

(56) References Cited

U.S. PATENT DOCUMENTS

| | | | | |
|---|---|---|---|---|
| 6,093,158 | A * | 7/2000 | Morris | 600/590 |
| 6,213,959 | B1 | 4/2001 | Kushida | |
| 6,261,238 | B1 * | 7/2001 | Gavriely | A61B 5/087 |
| | | | | 600/532 |
| 6,361,494 | B1 * | 3/2002 | Lindenthaler | 600/373 |
| 6,379,311 | B1 * | 4/2002 | Gaumond et al. | 600/529 |
| 6,580,944 | B1 | 6/2003 | Katz et al. | |
| 7,438,686 | B2 * | 10/2008 | Cho | A61B 5/0205 |
| | | | | 600/483 |
| 7,559,903 | B2 | 7/2009 | Moussavi et al. | |
| 2001/0018547 | A1 * | 8/2001 | Mechlenburg et al. | 600/15 |
| 2003/0004423 | A1 * | 1/2003 | Lavie et al. | 600/500 |
| 2003/0176788 | A1 * | 9/2003 | Crutchfield et al. | 600/437 |
| 2005/0080461 | A1 | 4/2005 | Stahmann et al. | |
| 2006/0279428 | A1 | 12/2006 | Sato et al. | |
| 2007/0150022 | A1 * | 6/2007 | Ujhazy et al. | 607/42 |
| 2009/0293886 | A1 * | 12/2009 | Dedrick et al. | 128/848 |
| 2013/0102917 | A1 | 4/2013 | Colbaugh et al. | |

FOREIGN PATENT DOCUMENTS

| | | |
|---|---|---|
| JP | 201082226 A | 4/2010 |
| WO | 199920339 A1 | 4/1999 |
| WO | 2005018737 A1 | 3/2005 |
| WO | 2011082199 A1 | 7/2011 |
| WO | 2012001621 A1 | 1/2012 |
| WO | 2012042453 A1 | 4/2012 |

OTHER PUBLICATIONS

Andrew Keong Ng et al; "Investigation of Obstructive Sleep Apnea Using Nonlinear Mode Interactions in Nonstationary Snore Signals", Annals of Biomedical Engineering, vol. 37, No. 9, Sep. 2009, pp. 1796-1806.
Fatima Cintra et al; "A Potential Biomarker for Obstructive Sleep Apnea", Chest 2011, Sleep Disorders vol. 139, No. 2, pp. 246-252.
Bi et al, "Clinical Significance of Acoustic Pharyngealmetry for Diagnosing Oshahs", Journal of Tongji University (Medical Science), vol. 27, No. 3, Jun. 2006, pp. 61-63 (With Translation).
Ng et al, "Investigation of Obstructive Sleep Apnea Using Nonlinear Mode Interactions in Nonstationary Snore Signals", Annals of Biomedical Engineering, vol. 37, No. 9, 2009, pp. 1976-1806.

* cited by examiner

METHOD AND APPARATUS FOR DIAGNOSING OBSTRUCTIVE SLEEP APNEA WITH AN AWAKE PATIENT

The present invention pertains to the diagnosis of obstructive sleep apnea, and, in particular, to apparatus and methods for collecting information from a patient that is awake and that can be used in diagnosing obstructive sleep apnea in the patient.

Obstructive sleep apnea (OSA) is a condition in which a subject experiences a decrease or complete stop in airflow while asleep, despite the subject continuing to try to breathe. These events occur when the muscles relax during sleep, causing soft tissue in the back of the throat to collapse and block the upper airway. This leads to partial reductions (known as hypopneas) and complete pauses (known as apneas) in breathing. An apnea event is defined as a cessation of airflow for at least 10 seconds during sleep. Hypopnea is defined as an abnormal respiratory event lasting at least 10 seconds with at least a 30 percent reduction in thoracoabdominal movement or airflow as compared to a baseline, with at least a 4 percent oxygen desaturation. Most apnea events last between 10 and 30 seconds, but some may persist for one minute or longer. This can lead to abrupt reductions in blood oxygen saturation, with oxygen levels falling as much as 40 percent or more in severe cases.

These apnea events cause the subject to wake briefly which restores normal breathing. As these apneas can occur tens or hundreds of times per night, the disruption caused results in the subject being excessively tired during the day.

A common measurement of sleep apnea is the apnea-hypopnea index (AHI). This is a number that represents the combined number of apneas and hypopneas that occur per hour of sleep. The following classification is frequently used:

AHI<5: No OSA/Healthy
5<AHI<15: Mild OSA
15<AHI<30: Moderate OSA
30<AHI Severe OSA Generally, obstructive sleep apnea is diagnosed in a sleep laboratory. However, most patients suffering from obstructive sleep apnea are never properly diagnosed since primary care physicians frequently deal with the symptoms of daytime fatigue and poor sleep by prescribing sleeping pills or similar medication. Physicians can be hesitant to send patients to a sleep laboratory immediately because of the high cost involved and the long waiting times. Usually patients are only sent when all other treatment attempts have failed and the patient keeps on complaining about bad sleep and daytime sleepiness. However, once a patient with suspected OSA is sent to a sleep laboratory, OSA is confirmed in around 85% of the cases.

OSA is diagnosed in a sleep laboratory with the help of "polysomnography" which is performed over one or more nights while the patient is asleep. Polysomnography can involve the use of an electroencephalogram (EEG), an electrocardiogram (ECG), an electroculogram (EOG), an electromyogram (EMG) and/or respiratory chest bands and the measurement of nasal airflow, blood oxygen levels and/or other physiological parameters. As a large number of sensors and devices are required for polysomnography, this procedure is not very comfortable or convenient for the patient.

Generally, the events of apnea and hypopnea in the polysomnography data are identified by a physician manually inspecting short intervals (roughly 30 seconds) of data, and individually rating the relevance of those intervals. Apnea events are characterized by the airflow through the patient's nasal passage stopping (or nearly stopping) while the thoracic and abdominal breathing movement continues. The number of identified events are counted and the average number of events per hour is used as an indicator of whether the patient has OSA and, if so, its severity. However, a substantial amount of effort is required to scan the data covering a whole night in order to detect and count all apnea and hypopnea events, and to determine the AHI value for a patient.

Alternative techniques for diagnosing OSA have been proposed that involve the investigation of the snoring sounds of a patient. One such technique is described in "Investigation of Obstructive Sleep Apnea Using Nonlinear Mode Interactions in Nonstationary Snore Signals" by Ng et al., *Annals of Biomedical Engineering*, Vol. 37, No. 9, September 2009, pp. 1796-1806. However, this technique again requires the patient to attend a sleep laboratory and to be monitored while they are sleeping.

Therefore, there is a need for a more efficient method and apparatus for diagnosing OSA screening that can be used while the patient is awake. Such a method and apparatus would allow more patients with suspected or possible OSA to be diagnosed and would increase the number of patients with OSA that receive appropriate treatment for their condition.

In one embodiment, an apparatus for use in diagnosing the presence of obstructive sleep apnea (OSA) in a patient is provided that includes a sensing module structured to measure a parameter indicative of a tremor in the patient's neck, tongue and/or throat muscles while the patient is awake, the parameter not uniquely being airflow through the patient's airway. The sensing module generates one or more electrical signals based on the measured parameter. The apparatus also includes a processor operatively coupled to the sensing module, the processor being structured to receive the one or more electrical signals, perform an analysis of the one or more electrical signals, and based on the analysis determine whether the tremor has a frequency in at least one predetermined frequency range that is indicative of OSA.

In another embodiment, an apparatus for use in diagnosing the presence of obstructive sleep apnea (OSA) in a patient is provided that includes a (i) first sensing module structured to measure a first parameter indicative of a tremor in the patient's neck, tongue and/or throat muscles while the patient is awake, the first sensing module generating one or more first electrical signals based on the measured first parameter and (ii) a second sensing module structured to measure a second parameter indicative of a tremor in the patient's neck, tongue and/or throat muscles while the patient is awake, the second parameter being different than the first parameter, the second sensing module generating one or more second electrical signals based on the measured second parameter. The apparatus also includes a processor operatively coupled to the first sensing module and the second sensing module, the processor being structured to: (i) receive the one or more first electrical signals, perform a first analysis of the one or more first electrical signals, and based on the first analysis make a first determination as to whether the tremor has a frequency in at least one predetermined frequency range that is indicative of OSA, (ii) receive the one or more second electrical signals, perform a second analysis of the one or more second electrical signals, and based on the second analysis make a second determination as to whether the tremor has a frequency in the at least one predetermined frequency range that is indicative of OSA, and (iii) determine whether the patient has OSA based on at least the first determination and the second determination.

In still another embodiment, a method of diagnosing the presence of obstructive sleep apnea (OSA) in a patient is provided that includes measuring a first parameter indicative of a tremor in the patient's neck, tongue and/or throat muscles while the patient is awake, determining based on the first parameter whether the tremor has a frequency in at least one predetermined frequency range that is indicative of OSA, evaluating whether the patient is likely for OSA using a second evaluation methodology, the second evaluation methodology not being based on measuring any parameters indicative of a tremor in the patient's neck, tongue and/or throat muscles, and determining that the patient has OSA only if at least the determining step determines that the tremor has a frequency in the at least one predetermined frequency range and the evaluating step determines that the patient is likely for OSA.

In another embodiment, a method of diagnosing the presence of obstructive sleep apnea (OSA) in a patient is provided that includes measuring a parameter indicative of a tremor in the patient's neck, tongue and/or throat muscles while the patient is awake, the parameter not being airflow through the patient's airway, determining based on the parameter whether the tremor has a frequency in at least one predetermined frequency range that is indicative of OSA, and determining that the patient has OSA if the determining step determines that the tremor has a frequency in the at least one predetermined frequency range.

In still another embodiment, a method of diagnosing the presence of obstructive sleep apnea (OSA) in a patient is provided that includes providing a predetermined amount of airflow resistance or level of pressure above or below atmospheric pressure to the patient to change the loading or bias pressure of the patient's breathing, following the providing step, measuring a parameter indicative of a tremor in the patient's neck, tongue and/or throat muscles while the patient is awake, determining based on the parameter whether the tremor has a frequency in at least one predetermined frequency range that is indicative of OSA, and determining that the patient has OSA if the determining step determines that the tremor has a frequency in the at least one predetermined frequency range.

In yet another embodiment, a method of diagnosing the presence of obstructive sleep apnea (OSA) in a patient is provided that includes measuring a first parameter indicative of a tremor in the patient's neck, tongue and/or throat muscles while the patient is awake, measuring a second parameter indicative of a tremor in the patient's neck, tongue and/or throat muscles while the patient is awake, the second parameter being different than the first parameter, making a first determination as to whether the tremor has a frequency in at least one predetermined frequency range that is indicative of OSA based on the first parameter, making a second determination as to whether the tremor has a frequency in the at least one predetermined frequency range that is indicative of OSA, based on the second parameter, and determining whether the patient has OSA based on at least the first determination and the second determination.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various FIGs. It is to be expressly understood, however, that the drawings are for the purpose of illustration and description only and are not intended as a definition of the limits of the invention.

Figure 3:
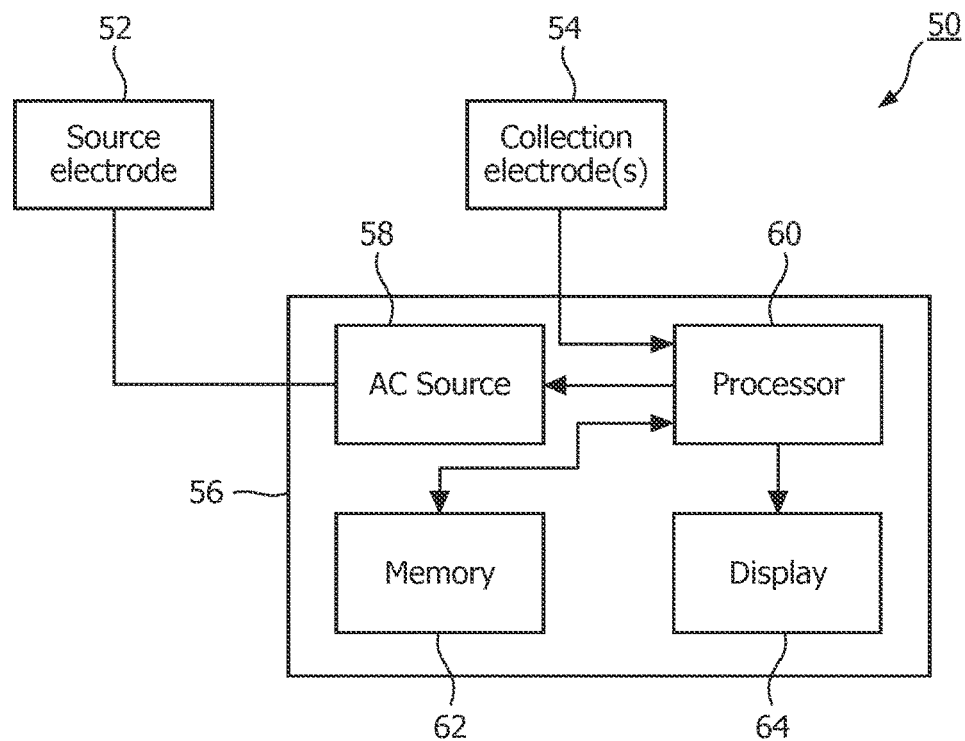
Figure 4:
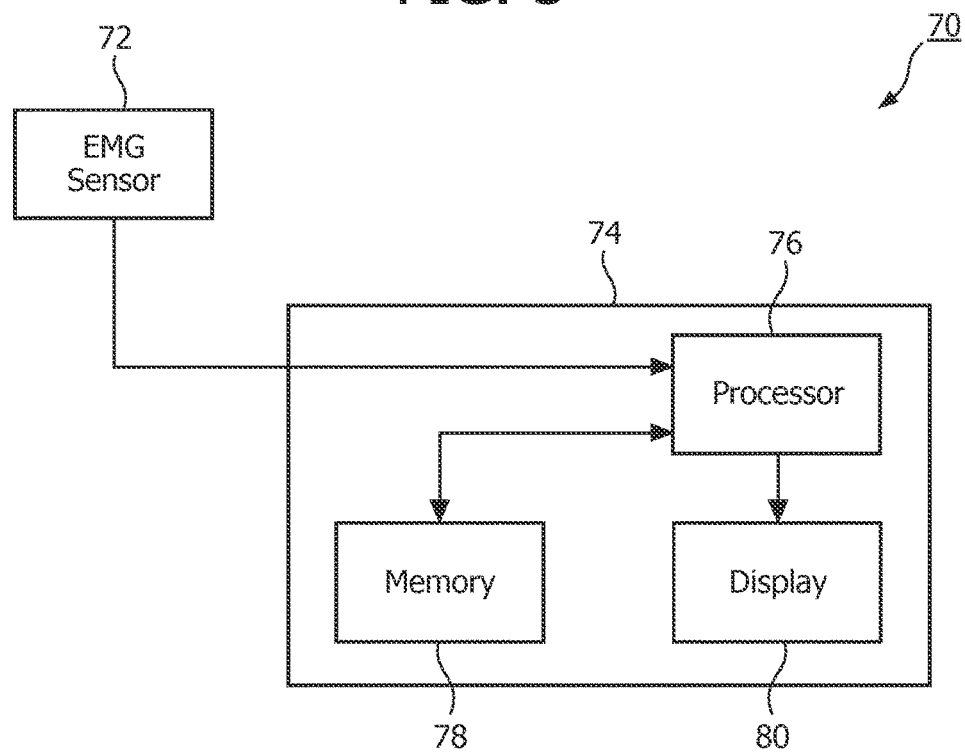
Figure 5:
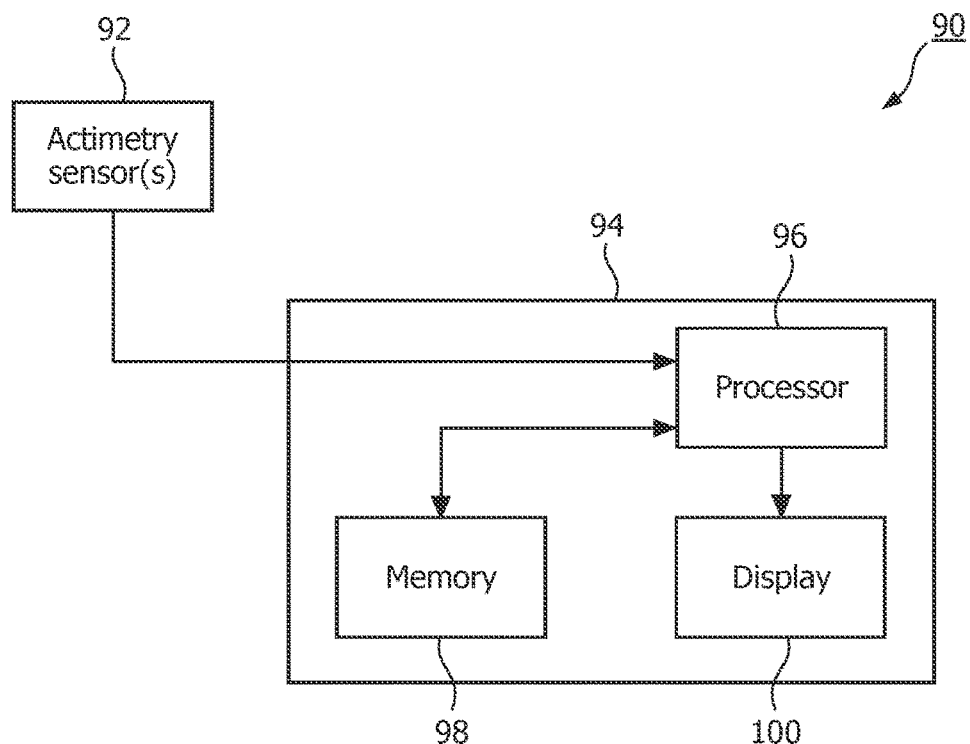
Figure 6:
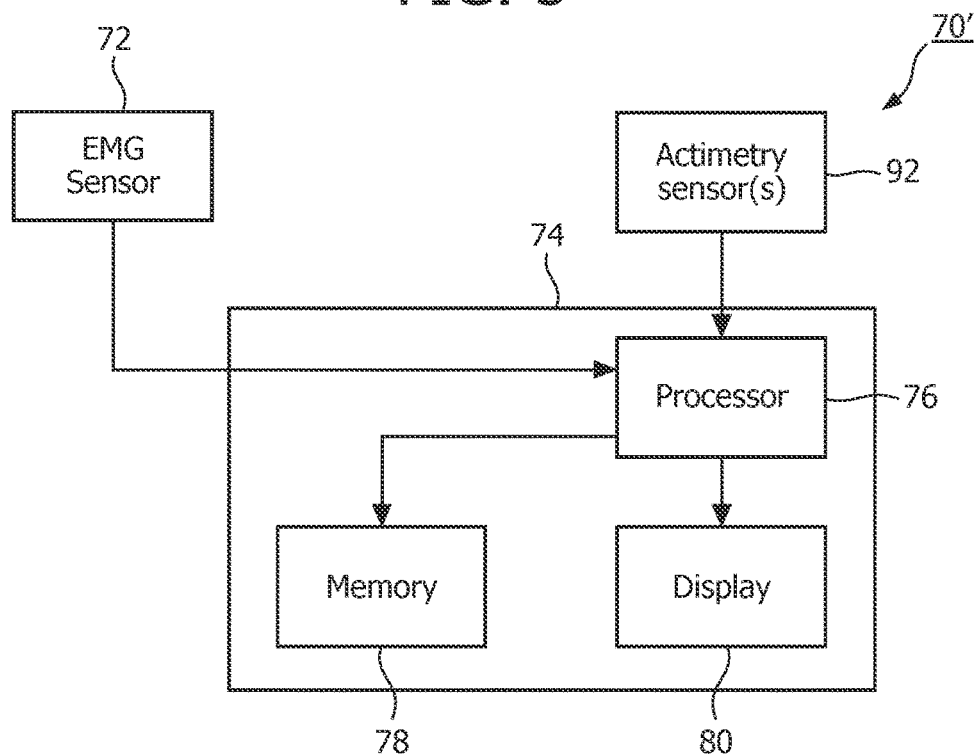
Figure 7:
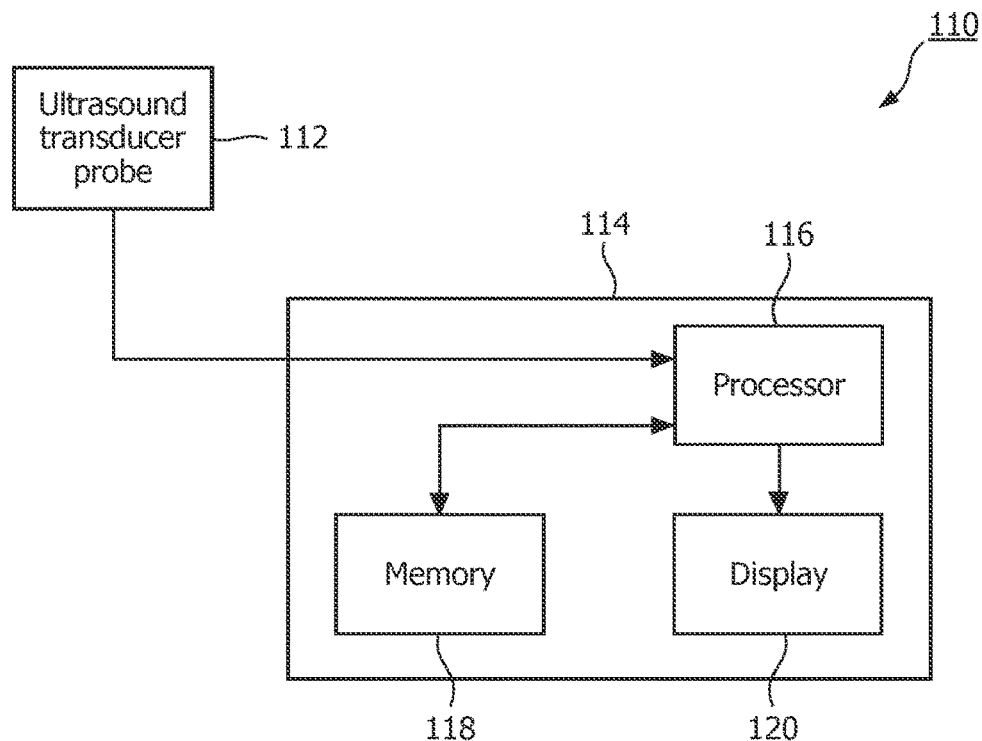
Figure 8:
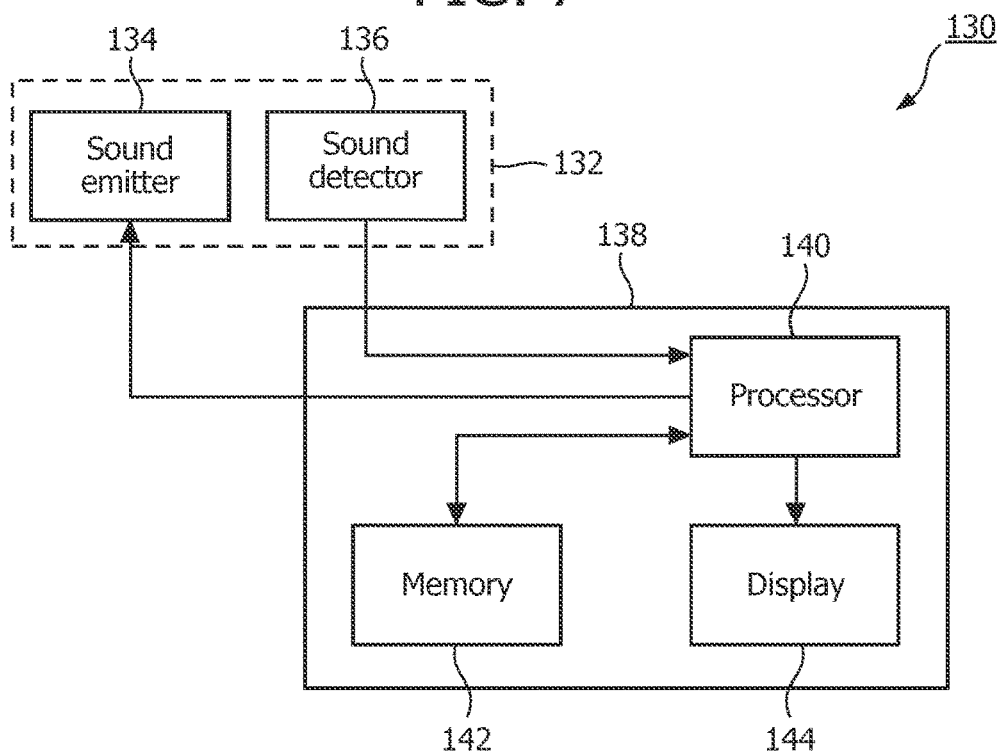
Figure 9:
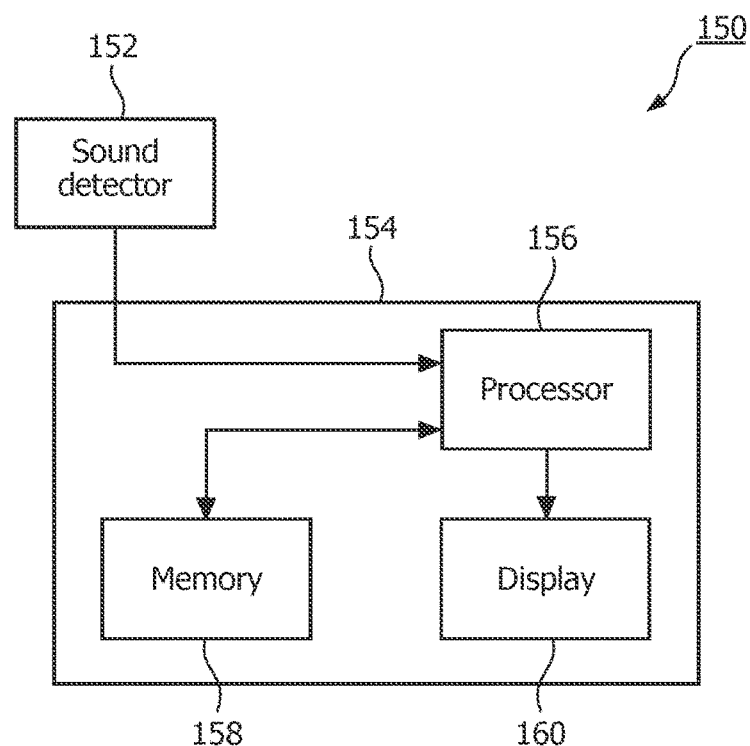
Figure 10:
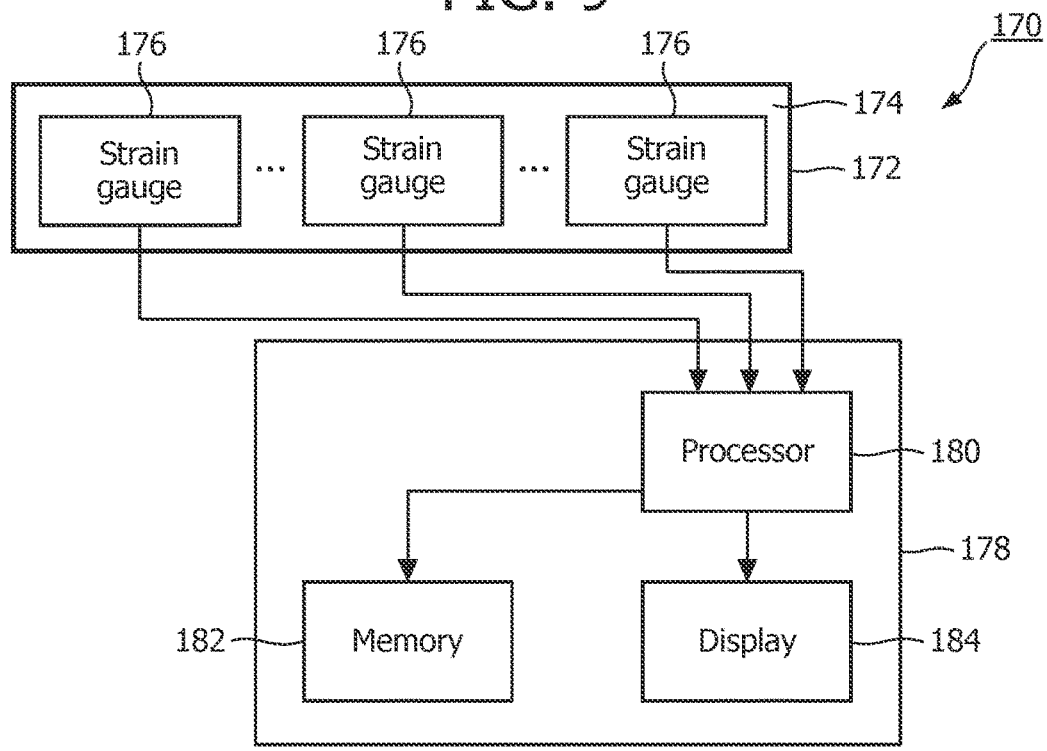
Figure 11:
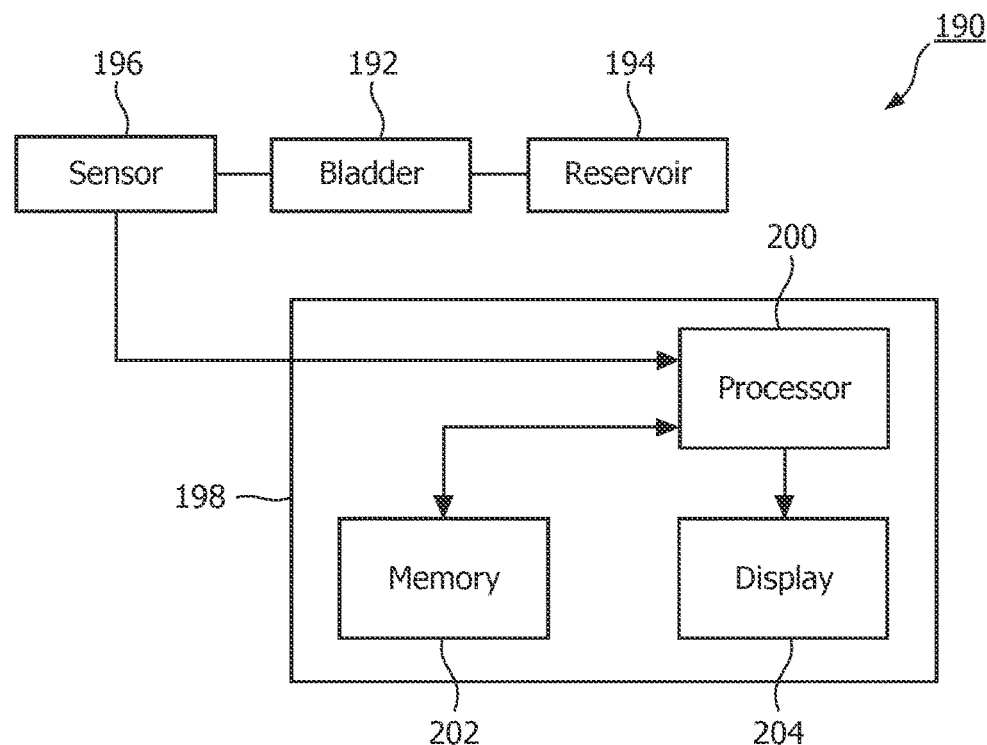
Figure 12:
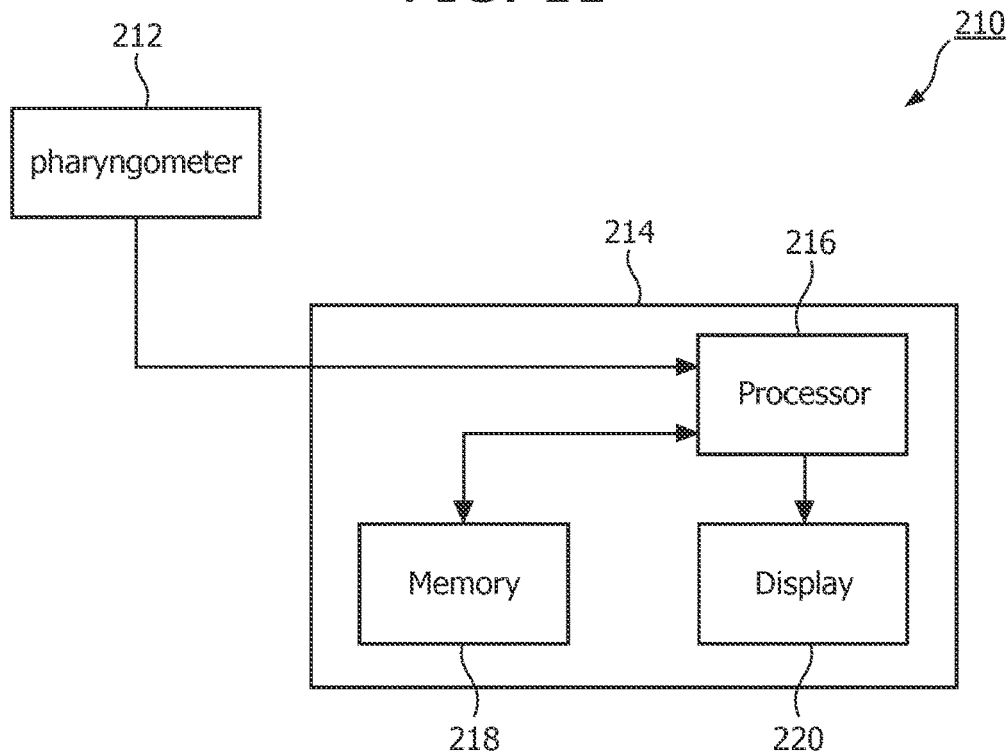
Figure 13:
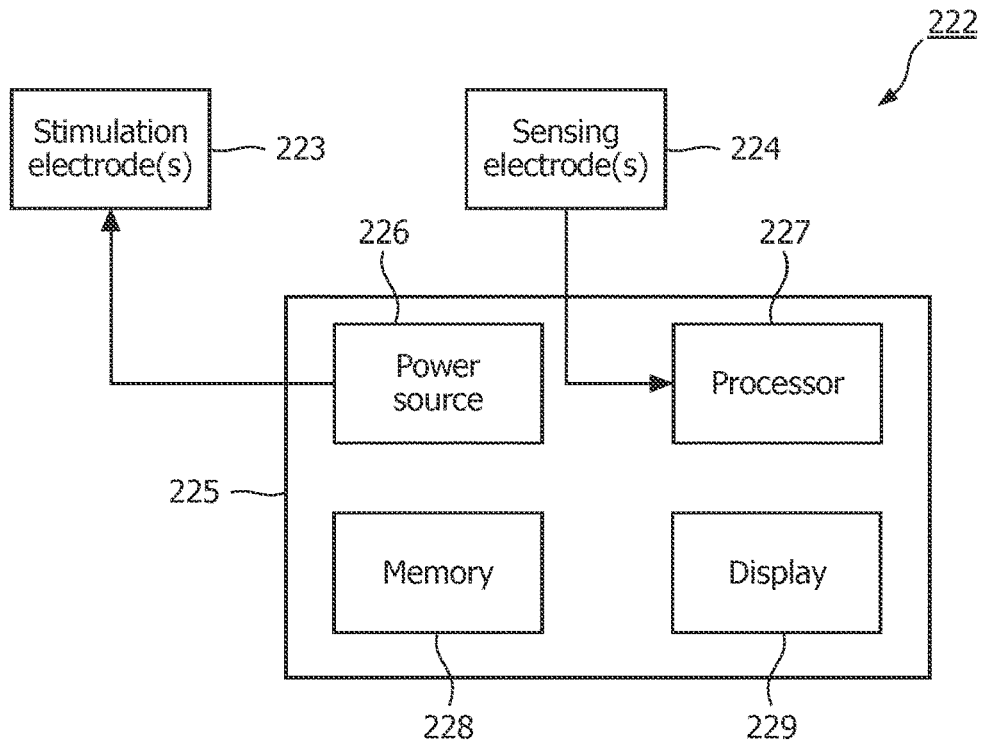
Figure 14:
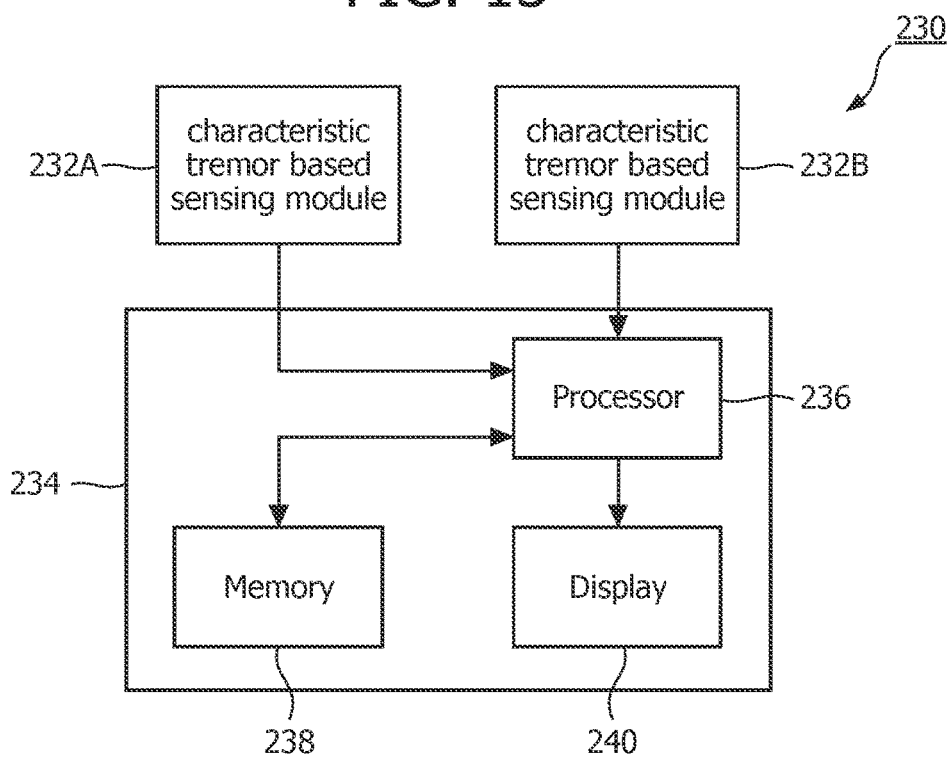
Figure 15:
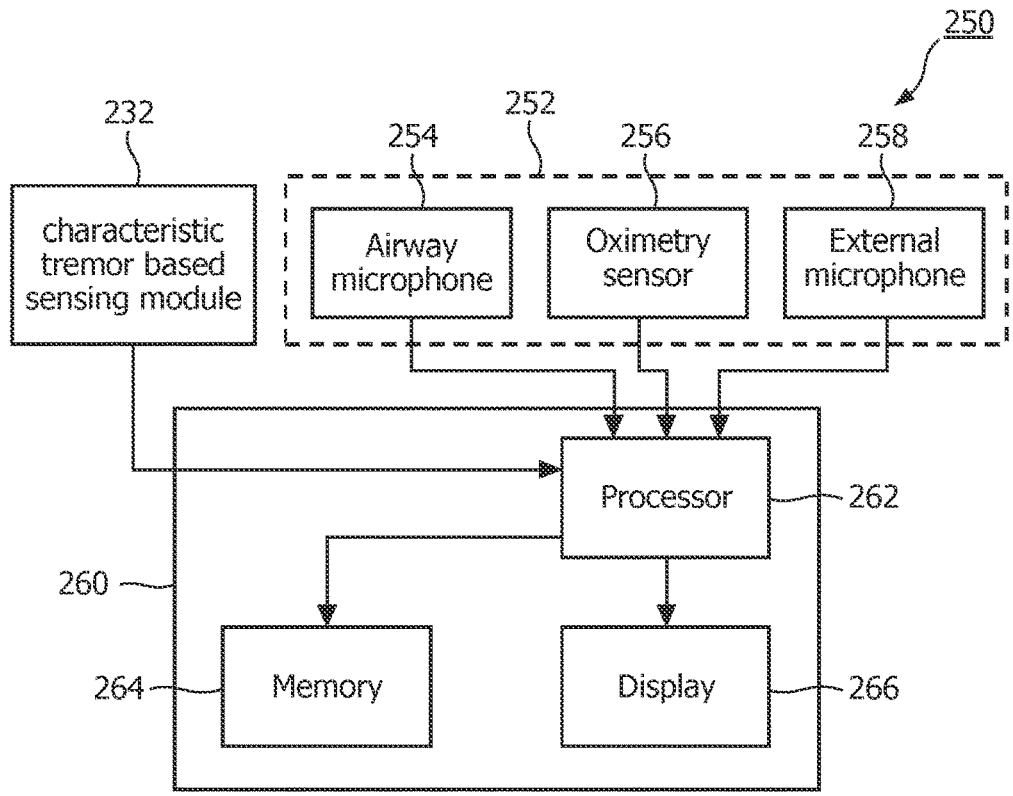
Figure 16:
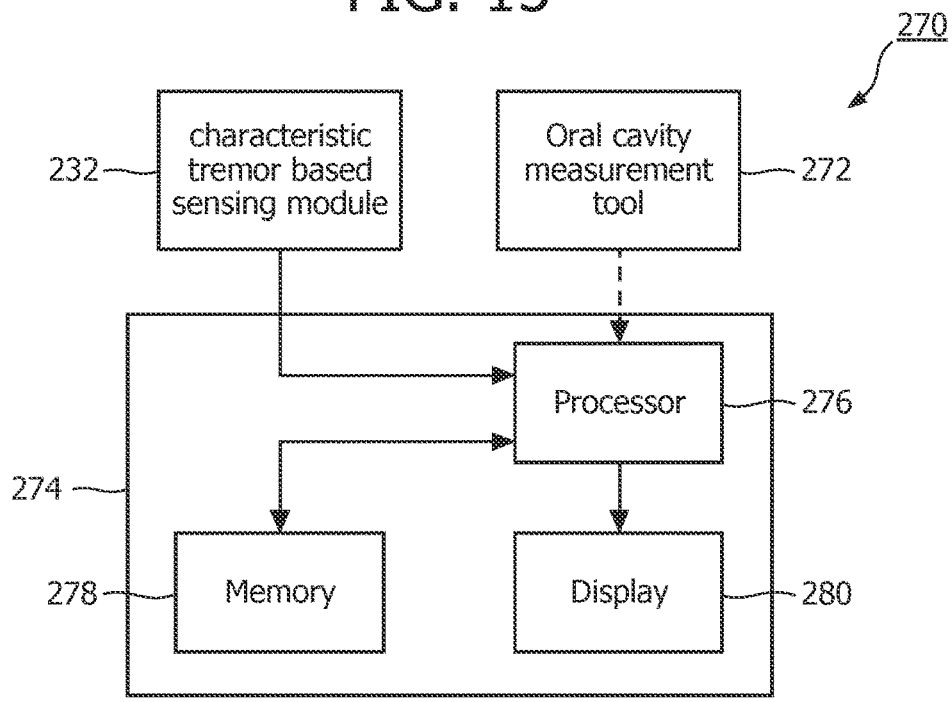
Figure 17:
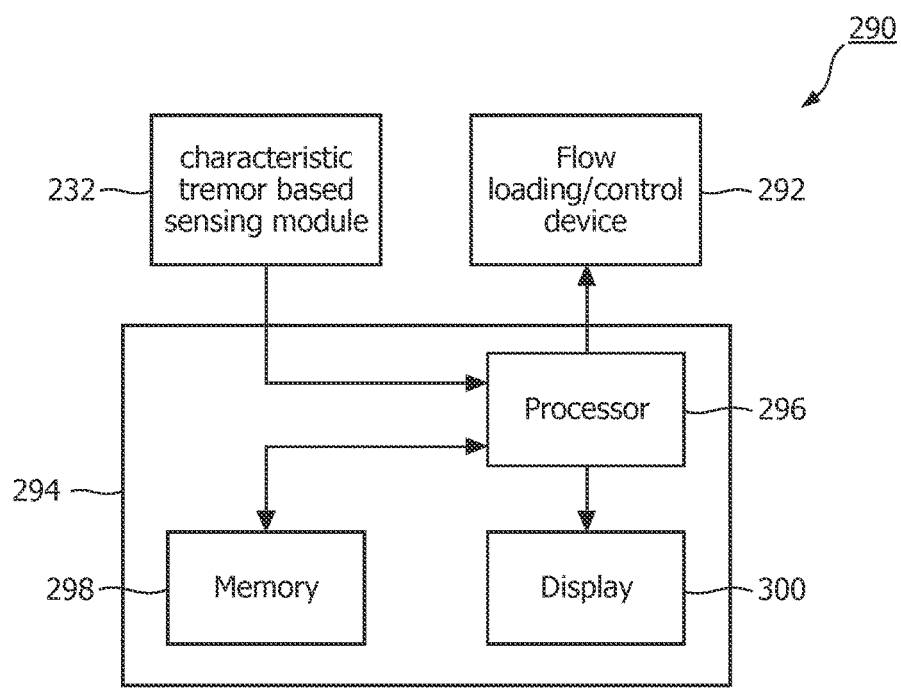

FIG. 3 a schematic diagram of an exemplary apparatus that can be used in the detection of OSA in a patient based on data that is collected from the patient while he or she is awake that is based on detecting modulated impedance in the patient's neck or throat area;

FIG. 4 a schematic diagram of an exemplary apparatus that can be used in the detection of OSA in a patient based on data that is collected from the patient while he or she is awake that is based on detecting throat muscle potential changes;

FIG. 5 a schematic diagram of an exemplary apparatus that can be used in the detection of OSA in a patient based on data that is collected from the patient while he or she is awake that employs actimetry;

FIG. 6 a schematic diagram of an exemplary apparatus that can be used in the detection of OSA in a patient based on motion/position data that is collected from the patient while he or she is awake that is based on both detecting throat muscle potential changes and actimetry;

FIG. 7 a schematic diagram of an exemplary apparatus that can be used in the detection of OSA in a patient based on data that is collected from the patient while he or she is awake that employs ultrasound measurements;

FIG. 8 a schematic diagram of an exemplary apparatus that can be used in the detection of OSA in a patient based on data that is collected from the patient while he or she is awake that employs sound generation and detection;

FIG. 9 a schematic diagram of an exemplary apparatus that can be used in the detection of OSA in a patient based on data that is collected from the patient while he or she is awake that employs airway sound detection;

FIG. 10 a schematic diagram of an exemplary apparatus that can be used to implement a method of OSA detection based on strain measurements;

FIG. 11 a schematic diagram of an exemplary apparatus that can be used to implement a method of OSA detection using a fluid filled bladder;

FIG. 12 a schematic diagram of an exemplary apparatus that can be used to implement a method of OSA detection using acoustic pharyngometry;

FIG. 13 a schematic diagram of an exemplary apparatus that can be used to implement a method of OSA detection using evoked potential/nerve conduction;

FIG. 14 a schematic diagram of an exemplary apparatus for detecting OSA that employs multiple methods and/or apparatus that detect the characteristic tremor associated with OSA;

FIGS. 15 and 16 are schematic diagrams of exemplary apparatus for detecting OSA that employ a combination of methods including one that is based on detecting the characteristic tremor associated with OSA and one that is not based on detecting the characteristic tremor associated with OSA; and FIG. 17 a schematic diagram of an exemplary apparatus for detecting OSA that employs a method that is based on detecting the characteristic tremor associated with OSA and a flow loading/control device.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Those afflicted with OSA have an increased compensatory muscular activation of the upper airway (the muscles of the neck, tongue and/or throat) during wakefulness. This muscular activation appears to be particularly prevalent in the genioglossus (GG) muscle, which is a muscle of the human body that runs from the chin to the tongue. The GG muscle is the major muscle responsible for protruding (or sticking out) the tongue. This increased compensatory muscular activation appears to be a product of an increased tonic activation of the muscle, combined with increased negative-pressure generation during inspiration.

In addition, the increased compensatory muscular activation during wakefulness results in a characteristic tremor in the upper airway. Testing performed by the assignee of the present invention has determined that the tremor exhibits a particular characteristic frequency that has an association with OSA and a disassociation with non-OSA patients. One such characteristic frequency has been found to be in the 30-40 Hz range, although other ranges are also possible. There is thus a lingering specific daytime signature of the assault caused by the sleeping disease OSA.

Furthermore, the assignee of the present invention has hypothesized that the tremor resulting from increased muscle (e.g., GG) activation modulates the respiratory airflow (at the characteristic frequency or frequencies) during wakefulness in those suffering from OSA, and has developed a system and method for diagnosing OSA that includes detecting the modulation of the respiratory airflow caused by the characteristic tremor. That system and method is described in detail in European patent application no. EP 10185347.1, entitled "Apparatus and Method for Collecting Information", the disclosure of which is incorporated herein by reference. That system and method is also described below.

Figure 1:
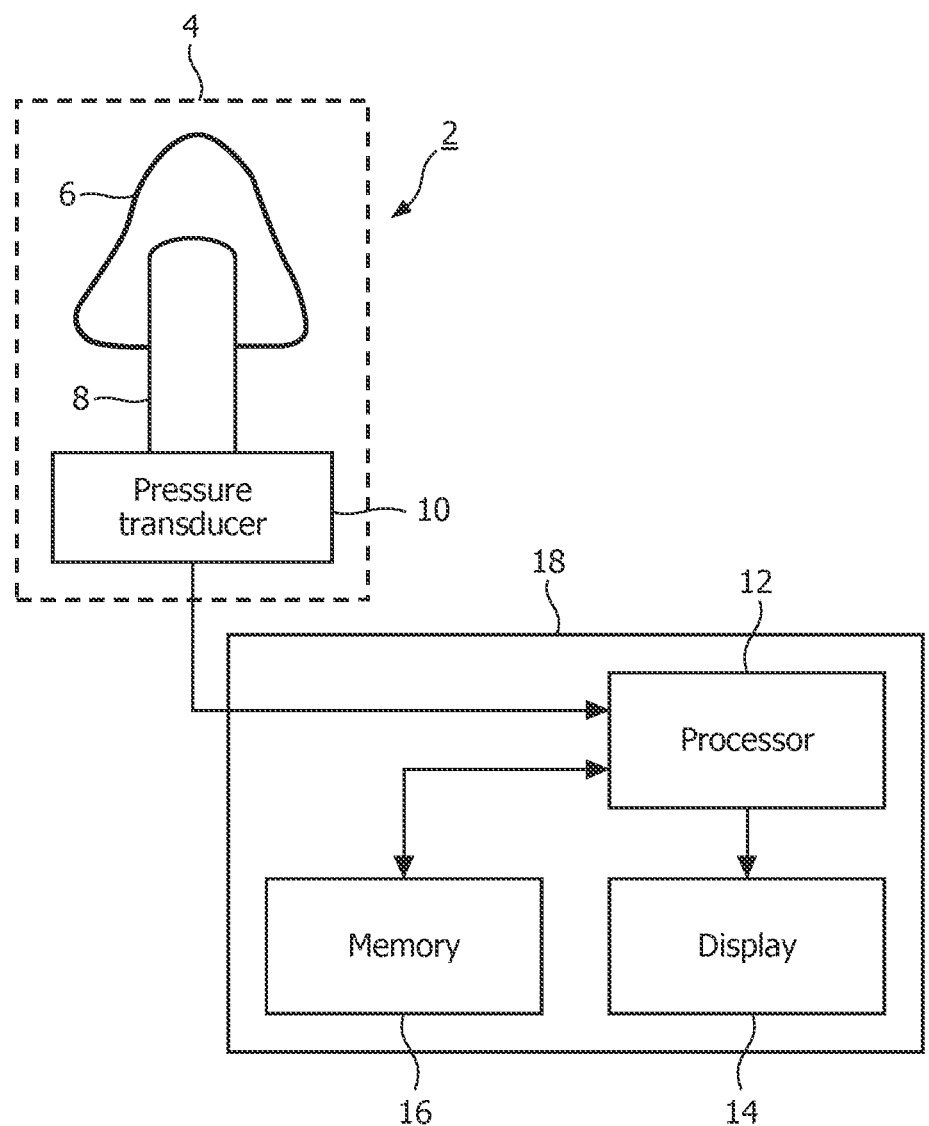
FIG. 1 is a schematic diagram of an exemplary apparatus that can be used in the detection of OSA in a patient based on airflow data that is collected from the patient while he or she is awake.

FIG. 1 shows an exemplary apparatus 2 of the above-described EP application that can be used in the detection of OSA in a patient based on data that is collected from the patient while he or she is awake. In the exemplary embodiment, the apparatus 2 comprises an air flow measuring device 4, such as a pneumotachograph, for providing measurements of the flow of air during inhalations and exhalations by a patient. As is known, a pneumotachograph 4 comprises a nasal mask, facial mask or mouthpiece 6 that can be worn by the patient, a pneumotachometer 8 that is connected to the nasal mask, facial mask or mouthpiece 6, that measures the flow of air being inhaled and exhaled by the patient through the nasal mask, facial mask or mouthpiece 6 and provides an output in terms of a differential pressure, and a pressure transducer 10 that is connected to the pneumotachometer 8 and that converts the differential pressure output into an electrical signal, preferably digital samples.

The electrical signal is provided from the pressure transducer 10 in the pneumotachograph 4 to a processor 12 where it is processed to determine information that can be used by a physician to determine whether the patient has a sleep-related breathing disorder, such as OSA. The processor 12 is connected to a display 14 that provides a visual indication of the result of the processing (such as the information to be used by the physician in diagnosing the patient, and/or, in some implementations, an indication of whether the patient has OSA or other breathing disorder). The processor 12 is also connected to a memory 16 that can store the electrical signals output from the pneumotachograph 4 prior to processing by the processor 12, as well as any result or results of the processing performed by the processor 12 on the electrical signals.

In the illustrated embodiment, the processor 12, display 14 and memory 16 are contained in a processing unit 18 that forms a separate unit to the pneumotachograph 4. In this case, the electrical signals from the pneumotachograph 4 can be provided to the processor 12 in the processing unit 18 via a connecting wire, wirelessly using WiFi, Bluetooth, etc., or by any other suitable means. However, in alternative implementations, the pneumotachograph 4 and processing unit 18 can be provided within a single housing. In either case, the apparatus 2 is preferably implemented as a lightweight device that can be easily held or worn by the patient during a testing procedure without causing the patient undue discomfort.

Although not shown in FIG. 1, it will be appreciated that the apparatus 2 (and in particular the processing unit 18) may include additional components, such as a user interface for allowing a user of the apparatus 2 to input commands and/or patient-specific data to the processor 12 and/or an internal power supply such as a battery if the apparatus 2 is to be operated independently of an external power supply.

In addition, in alternative embodiments, the pneumotachograph 4 can be replaced by an alternative means that can provide measurements of air flow, such as a nasal cannula.

Figure 2:
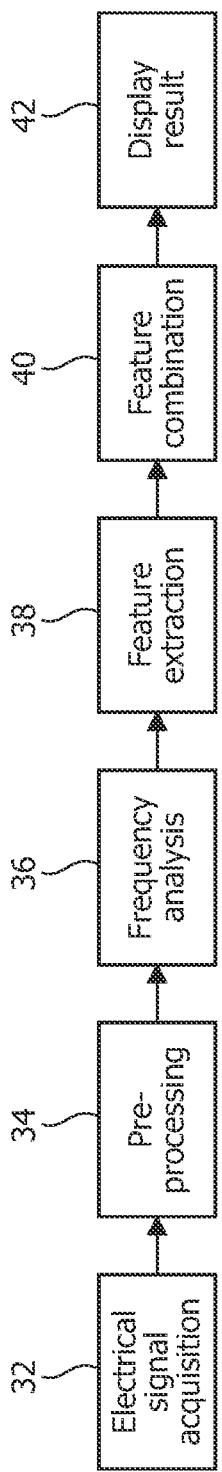
FIG. 2 is a functional diagram illustrating the operations performed by or in the apparatus of FIG. 1.

FIG. 2 is a functional diagram illustrating the operations performed by or in the apparatus 2. In a first step 32, electrical signals representing the air flow to and from the patient's lungs during breathing while the patient is awake are acquired from the pneumotachograph 4. The electrical signals preferably comprise digital samples representing the magnitude (i.e. rate) of the air flow at respective sampling instants. As suggested above, the first step 32 is performed while the patient is awake.

The air flow rate samples are passed to the processor 12 where they are processed to provide information relating to the breathing condition of the patient. In some embodiments this information is presented to a physician to assist the physician in diagnosing obstructive sleep apnea. In other embodiments, the processor 12 can further process the information to provide an indication of whether the patient has OSA, which can be output by the apparatus 2 to an operator (such as a physician), for example using the display 14.

It has been found that the raw sample data can contain artifacts, which can affect the quality of the analysis performed in subsequent processing steps. Therefore, it is desirable to provide a step that assesses the quality of the raw sample data and selects a subset of the data for one or more breathing cycles that are to be used in the subsequent processing steps. Thus, the first processing step performed by the processor 12 is a pre-processing step (step 34 in FIG. 2) in which the raw sample data is processed to identify N breathing cycles (with a single breathing cycle comprising a consecutive inhalation and exhalation) that are to be used in subsequent processing steps. Preferably, the N breathing cycles selected are those breathing cycles that best fit a mean breathing cycle for the patient. In one particular embodiment, N is 12, although N can take any positive integer value.

The selection of the N breathing cycles is, in the exemplary embodiment, performed as follows. Firstly, the raw sample data is separated into individual breathing cycles, and preferably individual inhalation and exhalation segments. The transition points between each inhalation and exhalation (i.e. where the patient starts to exhale after inhaling and exhaling after inhaling) can be easily identified from the zero-crossings in the sample data.

Next, the breathing cycles or individual inhalation and exhalation segments are filtered using one or more criteria, for example, a minimum length, the deviation from a mean length (in total and also separately for inhalation and exhalation segments) and deviation from a mean shape. The N cycles or segments best meeting the required criteria are then selected for further analysis by the processor 12.

In one embodiment of the invention, in order to reduce the amount of time that a patient has to be attached to the testing apparatus 2, the processor 12 can perform the pre-processing step while the data is being collected, and can provide an indication to the patient or other user of the apparatus 2 that the test can be stopped once the data for N breathing cycles has been collected.

After the preprocessing step, the processor 12 performs a frequency analysis step 36 in which the sample data is converted into the frequency domain and a mean frequency spectrum is calculated. In particular, a sliding window Fast Fourier Transform (FFT) is applied to each individual breathing cycle to give a frequency spectrum.

In some implementations, the sliding window FFT can be applied to each complete inhalation or exhalation segment. Alternatively, in other embodiments, the sliding window FFT is applied to only a part of each inhalation or exhalation segment around the peak air flow (i.e. where the air flow rate is at a local maximum). In other words, the sliding window FFT is applied at and around the samples where the peak air flow occurs during each inhalation and exhalation. It has been found that this narrow sliding window approach provides a better data set for use in subsequent analysis by the processor 12. The N frequency-transformed breathing cycles are then averaged to provide separate mean frequency spectrums for inhalation and exhalation.

It has been found that the frequency spectrum obtained from air flow sample data for patients with a breathing disorder, such as OSA, differs from the frequency spectrum obtained from healthy patients. For example, changes have been identified in certain frequency ranges or bands below 100 Hz, most notably the 18-22 Hz and 30-40 Hz frequency bands. In particular, there is an elevation in the 30-40 Hz frequency band and a reduction in the 18-22 Hz frequency band for a patient with OSA compared to a healthy patient. Similar characteristics have been found in the mean inhalation frequency spectrum.

Thus, the processor 12 extracts values for one or more parameters from the frequency spectrum or spectrums determined in the frequency analysis processing step 36. In particular, the value for at least one parameter is determined from the signals in one or more frequency bands covering frequencies that are below 100 Hz. Various different parameters can be extracted in the feature extraction step 38 according to the invention.

One parameter that can be extracted is the difference between the mean exhalation frequency amplitude in a first frequency band, for example the range of 20-50 Hz, or, more specifically, 25-45 Hz, or, even more specifically, 30-40 Hz (denoted $f_{ex30-40}$), and the mean exhalation frequency amplitude in a second frequency band, for example the range of 12-30 Hz, or, more specifically, 15-25 Hz, or, even more specifically, 18-22 Hz (denoted $f_{ex18-22}$). The parameter value can be given by $f_{ex30-40}$-$f_{ex18-22}$, and according to the observation described above, the value of the parameter for a healthy patient will generally be negative, whereas the value will generally be higher for a patient with OSA. Thus, the value of this parameter can be used by a physician or the apparatus 2 to diagnose whether the patient has OSA. It will be appreciated by those skilled in the art that a value for a similar parameter can be obtained from the difference between the mean inhalation frequency amplitude in these or similar frequency ranges.

Another parameter that can be extracted is the difference between the mean exhalation frequency amplitude in a third frequency band, for example the range of 0-20 Hz, or, more specifically, 0-15 Hz, or, even more specifically, 0-10 Hz (denoted $f_{ex0-10}$) and the mean inhalation frequency amplitude in the same or a similar frequency band, for example the range 0-20 Hz, or, more specifically, 0-15 Hz, or, even more specifically, 0-10 Hz (denoted $f_{in0-10}$). The parameter value can be given by $f_{ex0-10}$-$f_{in0-10}$. The value of the parameter will be generally close to zero for a healthy patient, whereas the value will generally be higher for a patient with OSA. Thus, as with the first parameter above, the value of this parameter can be used by a physician or the apparatus 2 to diagnose whether the patient has OSA.

A further parameter that can be extracted is the difference between the mean frequency amplitude in the range 0-100 Hz for inhalation or exhalation (denoted $f_{in0-100}$ or $f_{ex0-100}$ as appropriate) and a 'noise' level at frequencies above 100 Hz.

Those skilled in the art will appreciate that the mean exhalation or inhalation frequency amplitude in a particular frequency band can be obtained from the output of the frequency analysis step 36 by averaging the amplitude of the frequency domain signal in the specified frequency band.

It will also be appreciated that the invention is not limited to the extraction of the specific parameters set out above, and that information useful for characterizing the breathing condition of a patient can be obtained from various other parameters that can be readily contemplated by those skilled in the art. In particular, parameters can be extracted from frequency bands other than those specified above. Furthermore, it is not essential for the parameter or parameters to be based on the mean amplitude in a specified frequency band, since comparable results can be derived using other mathematical operations such as the area under the plot of the frequency spectrum in the frequency band or from the square of the amplitude.

In addition to extracting values for one or more parameters from the signals in the frequency domain, the processor 12 can extract values for other parameters from the time domain samples provided by the pneumotachograph 4 (whether the raw data or the data following the preprocessing step 34) during the feature extraction step 38. For example, the processor 12 can extract time-domain features such as mean breathing cycle length and mean ratio between the length of the inhalation and length of the exhalation Once the required parameter values have been extracted from the data, the processor 12 can either present the parameter values to a physician or other healthcare professional via the display 14 (or other visual output such as a printer-generated document) for use in assisting the physician to arrive at a diagnosis for the patient, or the processor 12 can perform a further processing step to combine the parameter values into a single useful score value. In this feature combination step 40, the processor 12 can combine the extracted values of multiple parameters into a single score that can be used to assist in the diagnosis of a breathing disorder, as it has been found that a score based on the value of a number of the parameters described above is more useful in the reliable diagnosis of a breathing disorder than individual parameter values.

In further embodiments, the score can also be based on other patient-related parameters, such as body-mass index (BMI), age, sex, Mallampati score, etc. which can be manually input to the apparatus 2 by the patient or operator.

The present inventors have conceived a number of alternative measurement devices and/or methods which may be used to detect the characteristic tremor described above and/or the volumetric changes of the airway structures resulting from the characteristic tremor described above. One or more of these alternative sensing devices and/or methods may be employed alone, in combination with the method of detecting the modulation of the respiratory airflow caused by the characteristic tremor described above, or in any combination, to improve the accuracy of the OSA diagnosis and/or assessment In accordance with one such alternative method, it has been hypothesized that the tremor resulting from increased muscle (e.g., GG muscle) activation modulates the impedance across the throat or jaw (at the characteristic frequency or frequencies) during wakefulness in those suffering from OSA. FIG. 3 shows an exemplary apparatus 50 that can be used in the detection of OSA in a patient based on data that is collected from the patient while he or she is awake that is based on detecting the modulated impedance described above. In the exemplary embodiment, the apparatus 50 comprises a source electrode 52 and one or more collection electrodes 54. Source electrode 52 and collection electrode(s) 54 are structured to be selectively positioned on opposing sides or separated surfaces of the patient's neck or head. Apparatus 50 also includes a main housing 56 which houses an alternating current (AC) source 58, a processor 60, a memory 62 and a display 64.

In operation, a small alternating current (e.g. 100 KHz, at less than 0.5 mA of current) is generated by AC source 58 and caused to flow from source electrode 52 to collection electrode(s) 54. The current and/or voltage signal's amplitude will be modulated by the movement (tremor) of the muscles of the throat (e.g., the GG muscle). The electrical signal collected by the collection electrode(s) 54 is provided to processor 60 which (using one or more software program routines) examines the amplitude of the received signal in order to identify the characteristic modulation (e.g., 30-40 Hz or some other frequency range or ranges) associated with OSA, if present, to determine whether the patient has OSA. The programmed processor 60 is connected to display 64, which provides a visual indication of the result of the processing. Processor 60 is also connected to memory 62 so that memory 62 can store the electrical signals collected by the collection electrode(s) 54 prior to processing by processor 60, as well as any result or results of the processing performed by processor 60 on the electrical signals. The blood flow pulse and respiration of the patient, as well as other parameters, may also be detected separately from the signal collected by the collection electrode(s) 54, and used for diagnostic purposes. In the exemplary embodiment, apparatus 50 is implemented as a lightweight device that can be easily held or worn by the patient during a testing procedure without causing the patient undue discomfort. Although not shown in FIG. 3, it will be appreciated that the apparatus 50 (and in particular the housing 56) may include additional components, such as a user interface for allowing a user of the apparatus 50 to input commands and/or patient-specific data to the processor 60 and/or an internal power supply such as a battery if the apparatus 50 is to be operated independently of an external power supply.

In accordance with another alternative method, it has been hypothesized that the tremor resulting from increased muscle (e.g., GG muscle) activation can be measured directly during wakefulness in order to identify the characteristic modulation (e.g., 30-40 Hz or some other frequency range or ranges) associated with OSA to determine whether the patient has OSA. In this method, the airway muscle movement nerve potential changes (i.e., electrical potential changes generated by muscles cells) are detected with an electromyogram (EMG) sensing technique in order to detect the characteristic modulation associated with OSA. FIG. 4 shows an exemplary apparatus 70 that can be used in the detection of OSA in a patient based on data that is collected from the patient while he or she is awake that is based on detecting throat muscle potential changes. In the exemplary embodiment, the apparatus 70 comprises an EMG sensor 72 that comprises two or more surface electrodes that are structured to be selectively placed in locations on the neck and/or head (e.g. right-left sides of the neck just under the mandible and/or lower, front-back of the neck, right-left sides of the jaw, cantered under the jaw with a return electrode on the face or neck, etc.). The EMG sensor 72 detects EMG signals indicative of hypoglossal nerve (CN XII) activation of the genioglossus (GG) muscle or other related nerves or muscles of the airway and head. As an alternative to surface electrodes as just described, although more invasive, EMG sensor 72 may comprise a needle electrode adapted to be inserted into muscle tissue for measuring intramuscular EMG. As seen in FIG. 4, apparatus 70 also includes a main housing 74 which houses a processor 76, a memory 78 and a display 80.

In operation, the EMG signals collected by EMG sensor 72 are provided to processor 76 which (using one or more software program routines) examines the signals in order to identify in the EMG signals the characteristic modulation (e.g., 30-40 Hz or some other frequency range or ranges) associated with OSA, if present, to determine whether the patient has OSA (the EMG signal will be a collection of muscle potential signals from all near-by muscle activity, so the characteristic frequency signal will be a repetitive modulation of at least a part of the signal energy). Processor 76 is connected to display 80, which provides a visual indication of the result of the processing. Processor 76 is also connected to memory 78 so that memory 78 can store the EMG signals prior to processing by processor 76, as well as any result or results of the processing performed by processor 76 on the EMG signals. In the exemplary embodiment, apparatus 70 is implemented as a lightweight device that can be easily held or worn by the patient during a testing procedure without causing the patient undue discomfort. Although not shown in FIG. 4, it will be appreciated that the apparatus 70 (and in particular the housing 74) may include additional components, such as a user interface for allowing a user of the apparatus 70 to input commands and/or patient-specific data to the processor 76 and/or an internal power supply such as a battery if the apparatus 70 is to be operated independently of an external power supply.

In accordance with another alternative method, the tremor resulting from increased muscle (e.g., GG muscle) activation is measured directly during wakefulness using actimetry (also known as actigraphy) in order to identify the characteristic modulation (e.g., 30-40 Hz or some other frequency range or ranges) associated with OSA to determine whether the patient has OSA. More specifically, in this method, actimetry is used to monitor the motion of the neck to identify the characteristic modulation. FIG. 5 shows an exemplary apparatus 90 that can be used in the detection of OSA in a patient based on data that is collected from the patient while he or she is awake that employs actimetry. In the exemplary embodiment, the apparatus 90 comprises one or more actimetry sensors 92 that are structured to be selectively placed in locations on the neck and/or head to detect the tremor motion of respiratory muscles. In the exemplary embodiment, each of the actimetry sensors 92 comprises a piezoelectric or other electronic or optical based accelerometer coupled to a filter which filters out undesirable signals, such as those due to external vibrations. The actimetry sensor(s) 92 generate electrical signals indicative of movement of the muscles of the neck, tongue and/or throat (e.g., the genioglossus (GG) muscle). As seen in FIG. 5, apparatus 90 also includes a main housing 94 which houses a processor 96, a memory 98 and a display 100.

In operation, the electrical signals generated by the actimetry sensor(s) 92 are provided to processor 96 which (using one or more software program routines) examines the signals in order to identify in the signals the characteristic modulation (e.g., 30-40 Hz or some other frequency range or ranges) associated with OSA, if present, to determine whether the patient has OSA. Processor 96 is connected to display 100, which provides a visual indication of the result of the processing. Processor 96 is also connected to memory 98 so that memory 98 can store the electrical signals generated by the actimetry sensor(s) 92 prior to processing by processor 96, as well as any result or results of the processing performed by processor 96 on the electrical signals generated by the actimetry sensor(s) 92. In the exemplary embodiment, apparatus 90 is implemented as a lightweight device that can be easily held or worn by the patient during a testing procedure without causing the patient undue discomfort. Although not shown in FIG. 5, it will be appreciated that the apparatus 90 (and in particular the housing 94) may include additional components, such as a user interface for allowing a user of the apparatus 90 to input commands and/or patient-specific data to the processor 96 and/or an internal power supply such as a battery if the apparatus 90 is to be operated independently of an external power supply.

FIG. 6 shows an exemplary apparatus 70' that can be used in the detection of OSA in a patient based on data that is collected from the patient while he or she is awake that is based on both detecting throat muscle potential changes and actimetry. Apparatus 70' is similar to apparatus 70 shown in FIG. 4, and thus like components are labeled with like reference numerals. In this embodiment, the EMG signals collected by EMG sensor 72 are examined as described elsewhere herein in order to identify the characteristic modulation (e.g., 30-40 Hz or some other frequency range or ranges) associated with OSA, if present, and the electrical signals generated by the actimetry sensor(s) 92 are analyzed and employed to remove unwanted motion-related artifacts from the EMG signals.

In accordance with still another alternative method, the tremor resulting from increased muscle (e.g., GG muscle) activation is measured directly during wakefulness using ultrasonic dimensional measurements in order to identify the characteristic modulation (e.g., 30-40 Hz or some other frequency range or ranges) associated with OSA to determine whether the patient has OSA. Tissue thickness measurements of the muscle could be indicative of apnea similar to the way that heart wall thickness is used in cardiology, and/or the muscle dimensions can be dynamically measured to detect the subject characteristic motion (e.g., 30-40 Hz motion) of the genioglossus and/or other airway patency muscles. The motion of the size of the tongue or throat or other airway structures may be measured in the same way to detect the modulation caused by increased compensatory muscular activation of the upper airway.

FIG. 7 shows an exemplary apparatus 110 that can be used in the detection of OSA in a patient based on data that is collected from the patient while he or she is awake that employs ultrasound measurements. In the exemplary embodiment, the apparatus 110 comprises an ultrasonic transducer probe 112, which, as is well known in the art, is structured to emit ultrasound waves that will pass through the body and detect returning echoes that are caused when the ultrasound waves strike objects within the body. These returning echoes are used to identify the size, shape and distance from the probe of those objects. Usually a gel is applied to lubricate the area of the skin which lies above the internal structures which must be scanned to enable the ultrasonic transducer probe 112 to slide around easily and to increase the conduction of the sound into the body.

In the exemplary embodiment, ultrasonic transducer probe 112 will generate electrical signals indicative of the dimensions and movement of the muscles of the neck, tongue and/or throat (e.g., the genioglossus (GG) muscle). As seen in FIG. 7, apparatus 110 also includes a main housing 114 which houses a processor 116, a memory 118 and a display 120.

In operation, the electrical signals generated by the ultrasonic transducer probe 112 based on the returned sound waves (echoes) are provided to processor 116 which (using one or more software program routines) examines the signals in order to identify in the signals the characteristic modulation (e.g., 30-40 Hz or some other frequency range or ranges) associated with OSA, if present, to determine whether the patient has OSA. Processor 116 is connected to display 120, which provides a visual indication of the result of the processing. Processor 116 is also connected to memory 118 so that memory 118 can store the electrical signals generated by the ultrasonic transducer probe 112 prior to processing by processor 116, as well as any result or results of the processing performed by processor 116 on the electrical signals generated by the ultrasonic transducer probe 112. In the exemplary embodiment, apparatus 110 is implemented as a lightweight device that can be easily held or worn by the patient during a testing procedure without causing the patient undue discomfort. Although not shown in FIG. 7, it will be appreciated that the apparatus 110 (and in particular the housing 114) may include additional components, such as a user interface for allowing a user of the apparatus 110 to input commands and/or patient-specific data to the processor 116 and/or an internal power supply such as a battery if the apparatus 110 is to be operated independently of an external power supply.

Apparatus 110 may also be used to make ultrasonic velocity measurements in order to detect the characteristic modulation of the airway (e.g., 30-40 Hz or some other frequency range or ranges) associated with OSA. The velocity of the tongue's surface or internal features would have an oscillation characteristic of the subject tremor motion described herein. The motion of the tongue or throat or other airway structures may be measured using ultrasound to detect the modulation caused by increased compensatory muscular activation of the upper airway. In particular, ultrasonic transducer probe 112 may be used to emit ultrasonic pulses and collect resulting reflections, with Doppler-based motion measurements being used to detect the characteristic motion (e.g., 30-40 Hz motion) of the genioglossus and/or other airway patency muscles in order to diagnose OSA.

In accordance with yet another alternative method, the tremor resulting from increased muscle (e.g., GG muscle) activation is measured during wakefulness using sound generation and detection in order to identify the characteristic modulation (e.g., 30-40 Hz or some other frequency range or ranges) associated with OSA to determine whether the patient has OSA. More specifically, in this method, a sound generator with a particular tone or more complex waveform is used to emit a sound into the patient's throat. Sounds that are emitted by the patient in response to the original sound are detected, and changes between the emitted sound and the detected sound are analyzed in order to determine whether the characteristic modulation associated with OSA is present.

FIG. 8 shows an exemplary apparatus 130 that can be used in the detection of OSA in a patient based on data that is collected from the patient while he or she is awake that employs sound generation and detection as just described. In the exemplary embodiment, the apparatus 130 includes a sound module 132 that includes a sound emitter 134 and a sound detector 136. Sound emitter 134 is a device that is structured to emit sonic (audible), subsonic or ultrasonic sounds (having a particular tone or more complex waveform), and may comprise, for example and without limitation, a small audio speaker and calibrated microphone, or a configuration similar to a professional room audio analyzer (which emits a tone or tones, static or time varying, to detect the sound absorption or resonant properties of a chamber or room). Sound detector 136 is a device that is structured to detect sounds that are generated by the patient in response to the sounds generated by sound emitter 134, and may comprise, for example and without limitation, a microphone. In addition, sound module 132 is structured to be selectively positioned near the outside of the mouth or in the mouth or throat, or selectively inserted down the throat and into the pharyngeal region of the patient. When positioned as described, sound detector 136 is configured to detect a resonance of one or more chambers of the airway. The presentation of various selected audio emissions also may be used to "probe" various parts of the respiratory system as well. As an example, the resonant frequency of the mouth cavity is different than the longer more narrow trachea, or the even more narrow bronchial passages. By selecting an emitted sound close to at least one resonant frequency of the trachea, the system will be more sensitive to movement or change of dimension of the trachea, and be less sensitive to that of the bronchial passages or mouth cavity. As seen in FIG. 8, apparatus 130 also includes a main housing 138 which houses a processor 140, a memory 142 and a display 144.

The mouth or trachea cavities of the patient are expected to be modulated by the characteristic tremor of the airway muscles described elsewhere herein. As a result, the resonant frequency amplitude of sounds that are emitted by the patient in response to the original sound will be modulated by small changes in the dimensions of the airway caused by the tremors. Thus, in operation, sound emitter 134 is caused to emit sounds as described elsewhere herein, and sound detector 136 detects the sounds that are generated by the patient in response thereto. The sound signals detected by sound detector 136 are provided to processor 140, which examines the signals in order to identify from the signals (and based on the originally emitted sounds) the characteristic modulation (e.g., 30-40 Hz or some other frequency range or ranges) associated with OSA, if present. Processor 140 is connected to display 144, which provides a visual indication of the result of the processing. Processor 140 is also connected to memory 142 so that memory 142 can store the sound signals detected by sound detector 136 prior to processing by processor 140, as well as any result or results of the processing performed by processor 140. In the exemplary embodiment, apparatus 130 is implemented as a lightweight device that can be easily held or worn by the patient during a testing procedure without causing the patient undue discomfort. Although not shown in FIG. 8, it will be appreciated that the apparatus 130 (and in particular the housing 138) may include additional components, such as a user interface for allowing a user of the apparatus 130 to input commands and/or patient-specific data to the processor 140 and/or an internal power supply such as a battery if the apparatus 130 is to be operated independently of an external power supply.

In accordance with another alternative method, the tremor resulting from increased muscle (e.g., GG muscle) activation is measured during wakefulness by detecting airway sounds in order to identify the characteristic modulation (e.g., 30-40 Hz or some other frequency range or ranges) associated with OSA to determine whether the patient has OSA. More specifically, the sound of air travelling through the airway (during patient respiration) will be modulated by the characteristic muscle movements associated with OSA described elsewhere herein, because as air passes through the airway, while breathing, turbulence is changed by the slight changes in throat dimension caused by the subject movements. This method employs common signal processing methods to detect the characteristic modulation (e.g., 30-40 Hz or some other frequency range or ranges) associated with OSA the breathing sounds.

FIG. 9 shows an exemplary apparatus 150 that can be used in the detection of OSA in a patient based on data that is collected from the patient while he or she is awake that employs airway sound detection as just described. In the exemplary embodiment, the apparatus 150 includes a sound detector 152 that is structured to detect airway sounds that are generated by the patient while breathing, and may comprise, for example and without limitation, a microphone. In addition, sound detector 152 is structured to be selectively positioned near the outside of the mouth or in the mouth or throat, or selectively inserted down the throat and into the pharyngeal region of the patient. As seen in FIG. 9, apparatus 150 also includes a main housing 154 which houses a processor 156, a memory 158 and a display 160.

In operation, sound detector 152 detects airway sounds that are generated by the patient while breathing. The sound signals detected by sound detector 152 are provided to processor 140, which (using one or more software program routines) examines the signals in order to identify from the signals the characteristic modulation (e.g., 30-40 Hz or some other frequency range or ranges) associated with OSA, if present. Processor 156 is connected to display 160, which provides a visual indication of the result of the processing. Processor 156 is also connected to memory 158 so that memory 158 can store the sound signals detected by sound detector 152 prior to processing by processor 156, as well as any result or results of the processing performed by processor 156. In the exemplary embodiment, apparatus 150 is implemented as a lightweight device that can be easily held or worn by the patient during a testing procedure without causing the patient undue discomfort. Although not shown in FIG. 9, it will be appreciated that the apparatus 150 (and in particular the housing 154) may include additional components, such as a user interface for allowing a user of the apparatus 150 to input commands and/or patient-specific data to the processor 156 and/or an internal power supply such as a battery if the apparatus 150 is to be operated independently of an external power supply.

In accordance with still another alternative method, the tremor resulting from increased muscle (e.g., GG muscle) activation is measured during wakefulness by detecting the strain caused thereby in order to identify the characteristic modulation (e.g., 30-40 Hz or some other frequency range or ranges) associated with OSA to determine whether the patient has OSA. FIG. 10 shows an exemplary apparatus 170 that can be used to implement such a method of OSA detection. The apparatus 170 includes a strain detector 172 that is structured to detect motion caused by the muscles of the neck, tongue and/or throat (e.g., the genioglossus (GG) muscle) by detecting strain caused by such motion. In the exemplary embodiment, strain detector 172 comprises a flexible substrate 174, made of, for example and without limitation, a polymer material, steel or another metal, an elastic material, or fiber composite material, on which one or more strain gauges 176 is/are attached. Flexible substrate 174 is structured to be fixed over its length or at its ends by an adhesive or mechanical holding arrangement against the skin or other structures of the head and/or neck or inside the mouth. Each strain gauge 176 may be, for example, a foil strain gauge, although other types of strain gauges may also be used. As is known in the art, a typical foil strain gauge consists of an insulating flexible backing which supports a metallic foil pattern. As the object to which the strain gauge is attached is deformed, the foil is deformed, causing its electrical resistance to change. This resistance change, usually measured using a Wheatstone bridge, is related to the strain by the quantity known as the gauge factor. As seen in FIG. 10, apparatus 170 also includes a main housing 178 which houses a processor 180, a memory 182 and a display 184.

In operation, the electrical strain signals generated by each strain gauge 176 in response to movements caused by the muscles of the neck, tongue and/or throat are provided to processor 180, which (using one or more software program routines) examines the strain signals in order to identify from the signals the characteristic modulation (e.g., 30-40 Hz or some other frequency range or ranges) associated with OSA, if present. Processor 180 is connected to display 184, which provides a visual indication of the result of the processing. Processor 180 is also connected to memory 182 so that memory 182 can store the strain signals prior to processing by processor 180, as well as any result or results of the processing performed by processor 180. In the exemplary embodiment, apparatus 170 is implemented as a lightweight device that can be easily held or worn by the patient during a testing procedure without causing the patient undue discomfort. Although not shown in FIG. 10, it will be appreciated that the apparatus 170 (and in particular the housing 178) may include additional components, such as a user interface for allowing a user of the apparatus 170 to input commands and/or patient-specific data to the processor 180 and/or an internal power supply such as a battery if the apparatus 170 is to be operated independently of an external power supply.

In addition, in connection with apparatus 170, or the other embodiments described herein, various restraining apparatus, such as, without limitation, a chin rest, may be used to restrain the motion of the head and body of the patient to remove unwanted artifacts. Also, various different patient positions, such as supine or erect positions, may be beneficial to signal to noise of the measurements made in the various embodiments described herein, or to enhance the effect or diminish the effect being measured.

In accordance with still another alternative method, the tremor resulting from increased muscle (e.g., GG) activation is measured during wakefulness by detecting the volumetric changes in the volume of or displacement of a fluid from a bladder in order to identify the characteristic modulation (e.g., 30-40 Hz or some other frequency range or ranges) associated with OSA to determine whether the patient has OSA. FIG. 11 shows an exemplary apparatus 190 that can be used to implement such a method of OSA detection. In the illustrated embodiment, the apparatus 190 includes a fluid (i.e. air or liquid) filled bladder 192 that is fluidly coupled to a reservoir 194. A sensor 196 is operatively coupled to bladder 192 and is configured to measure the amount of fluid that is displaced from the bladder 192 into the reservoir 194 as a result of forces acting thereon. In this embodiment, a flow sensor between the bladder and the reservoir, or a pressure sensor in the reservoir may be used to monitor the variation in volume of the bladder, the volume of which is being modulated by the motion of the neck and internal muscles. In an alternative embodiment, reservoir 194 is not present, and the sensor 196 is configured to measure the volumetric changes in the bladder 192 as a result of forces acting thereon. In this embodiment, the sensor 196 may be a pressure sensor. If the bladder 192 is relatively thin and conforms closely to the contour of the neck just below the mandible for instance and the outer surface away from the body is more rigid or thicker, then motion of the throat surface will translate to a small fluctuation of pressure within the bladder, which may be sensed by sensor 196.

As seen in FIG. 11, apparatus 190 also includes a main housing 198 which houses a processor 200, a memory 202 and a display 204.

In operation, bladder 192 (and reservoir 194, if present) is placed under the mandible, along/around the neck, or into the mouth of the patient (suitable attachment means may be employed, such as one or more straps). When bladder 192 is so positioned, forces caused by movement of the muscles of the neck, tongue and/or throat will act upon the bladder 192, and either cause some of the fluid to be displaced into reservoir 194, if present, or cause the internal volume of bladder to change. This will be sensed by sensor 196, and the electrical signals generated by sensor 196 are provided to processor 200, which (using one or more software program routines) examines the signals in order to identify from the signals the characteristic modulation (e.g., 30-40 Hz or some other frequency range or ranges) associated with OSA, if present. Processor 200 is connected to display 204, which provides a visual indication of the result of the processing. Processor 200 is also connected to memory 202 so that memory 202 can store the sensor signals prior to processing by processor 200, as well as any result or results of the processing performed by processor 200. In the exemplary embodiment, apparatus 190 is implemented as a lightweight device that can be easily held or worn by the patient during a testing procedure without causing the patient undue discomfort. Although not shown in FIG. 11, it will be appreciated that the apparatus 190 (and in particular the housing 198) may include additional components, such as a user interface for allowing a user of the apparatus 190 to input commands and/or patient-specific data to the processor 200 and/or an internal power supply such as a battery if the apparatus 190 is to be operated independently of an external power supply.

In accordance with another alternative method, the tremor resulting from increased muscle (e.g., GG muscle) activation is measured during wakefulness using acoustic pharyngometry in order to identify the characteristic modulation (e.g., 30-40 Hz or some other frequency range or ranges) associated with OSA to determine whether the patient has OSA. As is known in the art, acoustic pharyngometry is a dynamic test that determines dimensions of the oral airway past the glottis while the patient is breathing. In particular, acoustic pharyngometry uses an acoustic reflection technique to measure the cross-sectional area of at least a portion of the patient's upper airway during inspiration.

FIG. 12 shows an exemplary apparatus 210 that can be used to implement such an acoustic pharyngometry method of OSA detection. The apparatus 210 includes a pharyngometer 212 that comprises a sound source for generating sound pulses, two microphones for detecting sounds, a wave tube portion and a mouthpiece coupled to the wave tube portion. Apparatus 210 also includes a main housing 214 which houses a processor 216, a memory 218 and a display 220. In operation, pharyngometer 212 continuously causes sound pulses to be propagated from the sound source along the wave tube portion and into the airway of the patient through the mouthpiece. As the incident sound wave travels along the patient's airway, a reflection wave is generated due to the axial gradients in acoustic impedance within the airway. Both the incident and the reflected sound signals are recorded by the microphones in pharyngometer 212. These signals are output to processor 216 that uses these signals to determine a cross-sectional area of the patient's airway along at least a portion of the length of the patient's airway using a known technique. The processing of the incident and reflected sound waves from the airway by processor 216 provides an area distance curve representing the lumen from which minimal cross-sectional area and volume the patient's upper airway can be derived. For a more detailed discussion of an acoustic pharyngometer and its operation, please refer to the "Eccovision Acoustic Pharyngometry System Operator Manual," published by E. Benson Hood Laboratories, Inc., the contents of which are incorporated herein by reference. An example of a pharyngometer suitable for use as pharyngometer 212 is the device manufactured by Hood Industries under the trade name, "Eccovision Acoustic Pharyngometry System." It is to be understood, however, that other pharyngometer devices, including one microphone pharyngometers, can be used in the present invention.

According to a further aspect of the present embodiment, after processor 216 makes measurements of the dynamic state of the patient's upper airway as just described, processor 216 further analyzes those measurements in order to determine from them whether the dimensions of the patient's airway, at a point, set of points, or all along the length of the airway, are varying according to the characteristic modulation (e.g., 30-40 Hz or some other frequency range or ranges) associated with OSA. Processor 216 is connected to display 220, which provides a visual indication of the result of the processing. Processor 216 is also connected to memory 218 so that memory 218 can store the dimensional measurements prior to processing by processor 216, as well as any result or results of the processing performed by processor 216. In the exemplary embodiment, apparatus 210 is implemented as a lightweight device that can be easily held or worn by the patient during a testing procedure without causing the patient undue discomfort. Although not shown in FIG. 12, it will be appreciated that the apparatus 210 (and in particular the housing 214) may include additional components, such as a user interface for allowing a user of the apparatus 210 to input commands and/or patient-specific data to the processor 216 and/or an internal power supply such as a battery if the apparatus 210 is to be operated independently of an external power supply.

Furthermore, the measurements of the patient upper airway made by pharyngometer 212 in cooperation with processor 216 may be separately examined to detect airway dimensional characteristics (not based on the characteristic tremor described herein) that have been found to be indicative of OSA according to any of a number of methodologies known in the art. One such methodology is described in U.S. Pat. No. 6,379,311 to Gaumond et al., assigned to the assignee of the present invention and entitled "Breathing Disorder Prescreening Device and Method", the disclosure of which is incorporated herein by reference.

In accordance with another alternative method, the tremor resulting from increased muscle (e.g., GG muscle) activation modulates the impedance across the throat or jaw (at the characteristic frequency or frequencies) during wakefulness in those suffering from OSA is detected/measured using evoked potential/nerve conduction. Evoked potential/nerve conduction involves nerve potential sensing electrodes placed near or into a target nerve by a needle electrode, and a second electrode or mechanical stimulation electrode is applied to stimulate the target nerve or an up-stream nerve (i.e. another nerve site which innervates the target nerve that is being sensed). The reaction time, firing rate or amplitude of the target nerve firing in response to the stimulation is measured in an evoked potential measurement, and the propagation time and/or the intensity of reaction of the target nerve to the stimulation is measured in a nerve conduction measurement. In this embodiment, evoked potential may be used to measure the characteristic tremor/motion of the GG muscle or other muscles of the patient's neck, tongue and/or throat by looking for the 30-40 Hz (or other characteristic frequency) in the firing rate of individual or groups of nerves. The fatigue related motion of the GG muscle or other muscles of the patient's neck, tongue and/or throat will evoke the modulation to the measured rates. Nerve conduction may be used to demonstrate that the potential fatigue due to OSA assault alters the reaction time or intensity of nerve pulses transmitted to or along the GG muscle or other muscles of the patient's neck, tongue and/or throat and/or connected nerves.

FIG. 13 shows an exemplary apparatus 222 that can be used in the detection of OSA in a patient based on data that is collected from the patient while he or she is awake that is based on evoked potential/nerve conduction. In the exemplary embodiment, the apparatus 222 comprises one or more stimulation electrodes 223 and one or more sensing electrodes 224. Apparatus 222 also includes a main housing 225 which houses a power source 226 which drives the one or more stimulation electrodes 223, a processor 227, a memory 228 and a display 229.

In operation, the one or more stimulation electrodes 223 are caused to stimulate the target nerve or an up-stream nerve, and the reaction of the target nerve is measured by the one or more sensing electrodes 224. The electrical signals collected by the one or more sensing electrodes 224 is/are provided to processor 227. Processor 227 determines the reaction time, firing rate or amplitude of the target nerve firing in response to the stimulation in the case where evoked potential is employed, and the propagation time and/or the intensity of reaction of the target nerve to the stimulation is measured in the case where nerve conduction is employed. Processor 227 then analyzes those parameters (using one or more software program routines) in order to identify the characteristic modulation (e.g., 30-40 Hz or some other frequency range or ranges) associated with OSA, if present, to determine whether the patient has OSA. The programmed processor 227 is connected to display 229, which provides a visual indication of the result of the processing. Processor 227 is also connected to memory 228 so that memory 228 can store the electrical signals collected by the one or more sensing electrodes 224 prior to processing by processor 227, as well as any result or results of the processing performed by processor 227 on the electrical signals.

Thus a number of different apparatus and methods have been described herein for detecting OSA by detecting the characteristic tremor resulting from increased muscle (e.g., GG muscle) activation that is associated with OSA. In still further embodiments, two or more of those methods and/or apparatus are used in combination in order to detect OSA with increased accuracy. FIG. 14 shows an exemplary apparatus 230 for detecting OSA that employs multiple methods and/or apparatus that detect the characteristic tremor described herein. Apparatus 230 includes a first characteristic tremor based sensing module 232A and a second characteristic tremor based sensing module 232B. First characteristic tremor based sensing module 232A may be any of the sensing modules described herein in connection with FIGS. 1 and 3-12, and thus may be flow measuring device 4 (FIG. 2), electrodes 52 and 54 (FIG. 3), EMG sensor 72 (FIG. 4), actimetry sensor 92 (FIG. 5), EMG sensor 72 and actimetry sensor 92 (FIG. 6), ultrasound transducer probe 112 (FIG. 7), sound module 132 (FIG. 8), sound detector 152 (FIG. 9), strain detector 172 (FIG. 10), a bladder system including bladder 192 and sensor 196 (FIG. 11), pharyngometer 212 (FIG. 12), stimulation electrode(s) 223 and sensing electrode(s) 224 (FIG. 13). Second characteristic tremor based sensing module 232B may be any of the sensing modules just described that is different than first characteristic tremor based sensing module 232A. Apparatus 230 also includes a main housing 234 which houses a processor 236, a memory 238 and a display 240.

In operation, first and second characteristic tremor based sensing modules 232A, 232B will make measurements as described herein and in conjunction with processor 236 will determine whether the characteristic tremor can be identified based on those measurements (as also described herein). Processor 236 will then determine whether OSA is present based on that processing. In one, non-limiting embodiment, processor 236 will determine that OSA is present only if the characteristic tremor can be identified based on the measurements made by both first and second characteristic tremor based sensing modules 232A, 232B. In addition, although only two characteristic tremor based sensing modules 232 are shown in FIG. 14, it will be understood that that is meant to be exemplary only and that more than two such modules may be employed. In such a case, processor 236 may determine that OSA is present only if the characteristic tremor can be identified based on the measurements made by all of the characteristic tremor based sensing modules. Alternatively, processor 236 may determine that OSA is present if the characteristic tremor can be identified based on the measurements made by some predetermined percentage or fraction of the characteristic tremor based sensing modules (e.g., at least ½ or ⅔ of the modules).

Furthermore, rather than simply using frequency analysis to detect the characteristic tremor resulting from increased muscle (e.g., GG) activation that is associated with OSA as described herein, other types of waveform/signal analysis could also be used to detect the apnea signature, such as, without limitation, analysis of amplitude, area, and/or temporal or sequential patterns.

In still further embodiments, one or more of the methods and/or apparatus for detecting OSA by detecting the characteristic tremor resulting from increased muscle (e.g., GG muscle) activation that is associated with OSA is/are used in combination with an OSA detection method that is not based on detecting the characteristic tremor in order to detect OSA with increased accuracy. A number of exemplary combinations are described below.

FIG. 15 shows an exemplary apparatus 250 for detecting OSA that employs a combination as just described. Apparatus 250 includes a characteristic tremor based sensing module 232 as described elsewhere herein. Apparatus 250 also employs an acoustical OSA detection method as described in U.S. Pat. No. 7,559,903 to Moussavi et al., entitled "Breathing Sound Analysis For Detection of Sleep Apnea/Popnea Events", the disclosure of which is incorporated herein by reference. As described in greater detail in U.S. Pat. No. 7,559,903, the described method uses sounds transmitted through the walls of the lower neck (i.e. suprasternal notch) while breathing while the subject is either supine or sitting erect, and in particular processes breathing related sounds in the frequency range of 150-800 Hz. In connection therewith, apparatus 250 further includes a collector module 252. As seen in FIG. 15, collector module 252 includes airway microphone 254 for recording airway sounds, oximetry sensor 256 for collecting conventional SaO$_2$ data or other oximetry data (e.g., a known optical based sensor structured to be placed on the finger of the patient), and external microphone 258 for recording environmental sounds. As described in the '903 patent, airway microphone 254 may comprise a neck band with a microphone mounted in a chamber placed over the supra-sternal notch, or, alternatively, a wireless microphone inside the ear. The three sensors allow for simultaneous data acquisition of the sound signals and the SaO$_2$ data. Apparatus 250 also includes a main housing 260 which houses a processor 262, a memory 264 and a display 266.

As also described in detail in the '903 patent, processor 262 will de-noise the recorded sound, separate snoring sounds, estimate the flow acoustically, detect apnea and/or hypopnea episodes, and count the duration and the frequency of apnea and/or hypopnea episodes. More specifically, the signal processing of the sound signals has three stages. First an automated algorithm finds the artifacts (that normally appear as impulses in the signal) and removes them from further analyses. Secondly, the snoring sounds, if they exist, are identified and separated from the respiratory sounds. Finally, from the cleaned respiratory sounds, the entropy of the signal is calculated, the effect of heart sounds is removed, and apnea episodes are detected and identified using Otsu's thresholding method described in detail in the '903 patent.

In operation, characteristic tremor based sensing module 232 will make measurements as described herein and in conjunction with processor 262 will determine whether the characteristic tremor can be identified based on those measurements (as also described herein). Processor 262 will then determine whether OSA is present based on that processing and the processing done by processor 262 on the signals obtained by collection module 252 as just described. In one, non-limiting embodiment, processor 262 will determine that OSA is present only if the characteristic tremor can be identified based on the measurements made by the characteristic tremor based sensing module 232 and if the processor 262 also detects OSA based on the signals obtained by collection module 252. In addition, although only one characteristic tremor based sensing module 232 is shown in FIG. 15, it will be understood that that is meant to be exemplary only and that two or more such modules may be employed. In such a case, processor 262 may determine that OSA is present only if the characteristic tremor can be identified based on the measurements made by all of the characteristic tremor based sensing modules and if the processor 262 also detects OSA based on the signals obtained by collection module 252. Alternatively, processor 262 may determine that OSA is present if the characteristic tremor can be identified based on the measurements made by some predetermined percentage or fraction of the characteristic tremor based sensing modules (e.g., at least ½ or ⅔ of the modules) and if the processor 262 also detects OSA based on the signals obtained by collection module 252.

The measurements of the method of the '903 patent and those based on the characteristic tremor based sensing module(s) 232 are thought to be independent to a significant degree, since the physical signals measured in each have their source in two different mechanisms (i.e. muscle movement detection vs. airway breathing sounds most likely caused by airway shape or resistance), plus the frequency range of the two signals detected are significantly different.

FIG. 16 shows an exemplary apparatus 270 for detecting OSA that employs a combination of an OSA detection method that is based on detecting the characteristic tremor described herein and an OSA detection method that is not based on detecting the characteristic tremor described herein. Apparatus 270 includes a characteristic tremor based sensing module 232 as described elsewhere herein. Apparatus 270 also employs an OSA detection method based on oral cavity measurements as described in U.S. Pat. Nos. 6,048,322 and 6,213,959 to Kushida, entitled "Morphometric Measuring Tool" and "Morphometric Modeling System and Method", respectively, the disclosures of which are incorporated herein by reference. In connection therewith, apparatus 270 further includes an oral cavity measurement tool 272 as described in the '322 and '959 patents. Apparatus 270 also includes a main housing 274 which houses a processor 276, a memory 278 and a display 280.

Oral cavity measurement tool 272 is structured to measure a first value indicative of a distance between the highest point of the patient's palate and the patient's tongue, a second value indicative of an overlap of the upper and lower right central incisors, a third value indicative of a distance between a molar on the right side of the upper jaw and a molar on the left side of the upper jaw, and a fourth value indicative of a distance between a molar on the right side of the lower jaw and a molar on the left side of the lower jaw. Processor 276 is structured to receive those anatomical values (e.g., by manual input or electronic transfer (wired or wireless) from oral cavity measurement tool 272 if it is configured to do so) and determine a morphometric model value for the patient based on the anatomical values that is indicative of a likelihood that the patient suffers from OSA. In one embodiment, the morphometric model value is also based on the patient's neck circumference at the level of the cricothyroid membrane and the patient's BMI. The particulars of the morphometric model are described in detail in the '322 and '959 patents.

In operation, characteristic tremor based sensing module 232 will make measurements as described herein and in conjunction with processor 276 will determine whether the characteristic tremor can be identified based on those measurements (as also described herein). Processor 276 will then determine whether OSA is present based on that processing and the determined morphometric model value as just described. In one, non-limiting embodiment, processor 262 will determine that OSA is present only if the characteristic tremor can be identified based on the measurements made by the characteristic tremor based sensing module 232 and if the morphometric model value indicates a likelihood for OSA. In addition, although only one characteristic tremor based sensing module 232 is shown in FIG. 16, it will be understood that that is meant to be exemplary only and that two or more such modules may be employed. In such a case, processor 276 may determine that OSA is present only if the characteristic tremor can be identified based on the measurements made by all of the characteristic tremor based sensing modules and if the morphometric model value indicates a likelihood for OSA. Alternatively, processor 276 may determine that OSA is present if the characteristic tremor can be identified based on the measurements made by some predetermined percentage or fraction of the characteristic tremor based sensing modules (e.g., at least ½ or ⅔ of the modules) and if the morphometric model value indicates a likelihood for OSA.

In addition, findings of recent research studies show preliminary evidence that specific concentrations of substances in the blood, saliva, and/or urine indicate the likelihood of OSA in certain populations. For example, the amino acid cysteine may be a biomarker for the development of OSA in obese and nonobese patients. Results showed that cysteine plasma levels were higher in patients with OSA compared with the control subjects. A subgroup of lean patients (BMI<25) with OSA also had higher cysteine levels than the control subjects. Researchers conclude that cysteine is a potential biomarker for OSA and that obesity does not influence its function as a biomarker. See, for example, Chest 2011; 139(2):246-252.

Finally, it should be understood that OSA detection methods that are not based on detecting the characteristic tremor other than those specifically described herein may also be employed.

In still further embodiments, the use of breath flow loading/control to precipitate or enhance/intensify tremors (or damp-out the tremors) may be used for measurement. FIG. 17 shows an exemplary apparatus 290 for detecting OSA that employs such breath flow loading/control. Apparatus 290 includes a characteristic tremor based sensing module 232 as described elsewhere herein. Apparatus 290 also includes a flow loading/control device 292 that is structured to be placed over the nasal openings and/or mouth of the patient, and which provides a predetermined amount of airflow resistance or level of pressure above/below atmospheric pressure to change the loading and/or bias pressure of the patient's breathing. The parameters of resistance and pressure may vary differently in the inspiratory and expiratory phases of respiration, or any time along the respiratory cycle. This change of ambient flow and/or pressure challenges or aids the breathing of the patient, enhancing or diminishing the lingering effects of OSA being measured by characteristic tremor based sensing module 232 described elsewhere herein. A number of embodiments of a suitable exemplary flow loading/control device 292 are described in U.S. Provisional Patent Application No. 61/361,037, assigned to the assignee of the present invention and entitled "System and method for Performing Respiratory Diagnostics", the disclosure of which is incorporated herein by reference. Apparatus 290 also includes a main housing 294 which houses a processor 296, a memory 298 and a display 300. In the illustrated embodiment, flow loading/control device 292 is provided as an integral part of apparatus 290 coupled to main housing 294 and controlled by processor 296. It should be understood, however, that flow loading/control device 292 could also be a separate device separate from main housing 294 and simply used in conjunction with characteristic tremor based sensing module 232.

In operation, flow loading/control device 292 is first placed over the nasal openings and/or mouth of the patient, and caused to provide a predetermined amount of airflow resistance or level of pressure above/below atmospheric pressure to change the loading and/or bias pressure of the patient's breathing in order to enhance/intensify tremors. Then, characteristic tremor based sensing module 232 is used to make measurements as described herein. Processor 296 then determines whether the characteristic tremor associated with OSA can be identified based on those measurements (as also described herein). Flow loading/control device 292 may be used with any of the particular embodiments described herein.

In addition to hyper-excited muscle activity, it is also possible to look for a subdued response to breathing challenges or other physiological functional challenges (e.g. speech, tone formation, swallowing, whistling, tongue movements, etc.), in cases where the muscle is fatigued sufficiently to not be up to the challenge. The range of sensing and detecting methods described herein may be used to monitor variations caused by this subdued physical response.

Standard questionnaires or physiologic assessment tools (e.g. Berlin Questionnaire for OSA, Epworth Sleepiness Scale questionnaire for daytime sleepiness, Mallampati throat opening classification, BANG, BANG-STOP, etc.) may be administered in conjunction with or be integrated into the functionality of the embodiments described herein in order to increase sensitivity and/or specificity of the OSA assessment. Parameters from these standard assessment tools may be entered through a user interface as describe herein, and the data may be mathematically combined with the measured sensory data of the embodiments described herein to produce an improved assessment predicting OSA.

The signals and detection methods described herein may also be applied during sleep as part of a PSG diagnostic session, which could potentially provide additional information to be used in the diagnostic/phenotypical assessment of the patient. In addition, the sensors/sensing modules and diagnostic methods could be incorporated into other devices such as a cannula or mask which are primarily used for therapy.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An apparatus for use in determining whether a tremor in a patient's neck, tongue and/or throat muscles has a frequency in at least one predetermined frequency range that is indicative of obstructive sleep apnea (OSA) in the patient, the apparatus comprising:
    a first sensing module, the first sensing module configured to measure a first parameter indicative of the tremor in the patient's neck, tongue and/or throat muscles while the patient is awake, the first parameter not being airflow through the patient's airway, the first sensing module generating one or more electrical signals based on the measured first parameter while the patient is awake, wherein the first sensing module comprises a velocity sensor configured to measure velocity of a surface of the tongue, and wherein the first parameter comprises the velocity of the surface of the tongue caused by the tremor;
    a processor operatively coupled to the first sensing module, the processor being configured to:
        receive the one or more electrical signals for a plurality of breathing cycles of the patient,
        select a subset of the plurality of breathing cycles that best fit a mean breathing cycle for the patient, wherein selecting the subset includes filtering the plurality of breaths based on a minimum length of the breathing cycles and selecting the breathing cycles having the minimum length,
        perform an analysis of the one or more electrical signals from the subset, and
        based on the analysis determine whether the tremor has a frequency in the at least one predetermined frequency range that is indicative of OSA, the at least one predetermined frequency range being associated with and characteristic of an increased compensatory muscular activation of the upper airway of the patient during wakefulness.

2. The apparatus according to claim 1, wherein the at least one predetermined frequency range is below 100 Hz.

3. The apparatus according to claim 2, wherein the at least one predetermined frequency range is 30-40 Hz.

4. The apparatus according to claim 1, further comprising:
    a second sensing module structured to measure a second parameter indicative of the tremor in the patient's neck, tongue and/or throat muscles while the patient is awake, the second parameter not being airflow through the patient's airway, wherein the second sensing module comprises an AC source, a source electrode, and one or more collection electrodes structured to be selectively positioned on separated surfaces of the patient's neck or head, wherein an alternating current generated by the AC source flows from the source electrode, wherein the second parameter comprises a modulated electrical signal collected by the one or more collection electrodes, the modulated electrical signal being modulated by the tremor, and wherein the processor is operatively coupled to the second sensing module and configured to:

perform an analysis of the modulated electrical signals from the source electrode and the one or more collection electrodes, and based on the analysis determine whether the tremor has a frequency in the at least one predetermined frequency range that is indicative of OSA.

5. The apparatus according to claim 1, further comprising:
a second sensing module configured to measure a second parameter indicative of the tremor in the patient's neck, tongue and/or throat muscles while the patient is awake, the second parameter not being airflow through the patient's airway, wherein the second sensing module comprises an EMG sensor, wherein the second parameter comprises muscle potential changes in the patient's neck, tongue and/or throat muscles caused by the tremor, and wherein the processor is operatively coupled to the second sensing module and configured to:

perform an analysis of the muscle potential changes caused by the tremor, and based on the analysis determine whether the tremor has a frequency in the at least one predetermined frequency range that is indicative of OSA.

6. The apparatus according to claim 1, further comprising:
a second sensing module configured to measure a second parameter indicative of the tremor in the patient's neck, tongue and/or throat muscles while the patient is awake, the second parameter not being airflow through the patient's airway, wherein the second sensing module comprises an actimetry sensor configured to be selectively positioned on the patient's neck or head, wherein the processor receives actimetry signals from the actimetry sensor and uses the actimetry signals to remove motion artifacts from the one or more electrical signals when performing an analysis of the one or more electrical signals.

7. The apparatus according to claim 1, wherein the velocity sensor comprises an ultrasonic transducer probe configured to emit ultrasound waves that will pass through the patient's body and detect returning echoes that are generated responsive to the emitted ultrasound waves, wherein the one or more parameters further comprise the returning echoes.

8. The apparatus according to claim 1, further comprising:
a second sensing module configured to measure a second parameter indicative of the tremor in the patient's neck, tongue and/or throat muscles while the patient is awake, the second parameter not being airflow through the patient's airway, wherein the second sensing module comprises a sound module that includes a sound emitter and a sound detector, wherein the sound module to be selectively positioned near the outside of the patient's mouth or in the patient's mouth or throat or selectively inserted down the patient's throat and into the patient's pharyngeal region, wherein the sound emitter is configured to emit first sounds and the sound detector configured to detect second sounds that are generated in response to the first sounds, and wherein the second parameter comprises the second sounds caused by the tremor, and wherein the processor is operatively coupled to the second sensing module and configured to:

perform an analysis of the second sounds caused by the tremor, and based on the analysis determine whether the tremor has a frequency in the at least one predetermined frequency range that is indicative of OSA.

9. The apparatus according to claim 1, further comprising:
a second sensing module configured to measure a second parameter indicative of the tremor in the patient's neck, tongue and/or throat muscles while the patient is awake, the second parameter not being airflow through the patient's airway, wherein the second sensing module comprises a sound detector that is configured to detect airway sounds that are generated by the patient while breathing, and wherein the second parameter comprises the airway sounds caused by the tremor, and wherein the processor is operatively coupled to the second sensing module and configured to:

perform an analysis of the airway sounds caused by the tremor, and based on the analysis determine whether the tremor has a frequency in the at least one predetermined frequency range that is indicative of OSA.

10. The apparatus according to claim 1, further comprising:
a second sensing module configured to measure a second parameter indicative of the tremor in the patient's neck, tongue and/or throat muscles while the patient is awake, the second parameter not being airflow through the patient's airway, wherein the second sensing module comprises a strain detector that is configured to be selectively positioned on the patient's neck and to detect strain resulting from motion caused by the muscles of the patient's neck, tongue and/or throat, and wherein second parameter comprises the strain caused by the tremor, and wherein the processor is operatively coupled to the second sensing module and configured to:

perform an analysis of the strain caused by the tremor, and
based on the analysis determine whether the tremor has a frequency in the at least one predetermined frequency range that is indicative of OSA.

11. The apparatus according to claim 10, wherein the strain detector comprises a flexible substrate having one or more strain gauges attached thereto.

12. The apparatus according to claim 1, further comprising:
a second sensing module configured to measure a second parameter indicative of the tremor in the patient's neck, tongue and/or throat muscles while the patient is awake, the second parameter not being airflow through the patient's airway, wherein the second sensing module comprises a fluid filled bladder structured to be positioned on or in the head, neck or mouth and a sensor operatively coupled to bladder, wherein the sensor is configured to measure an amount of fluid displaced from the bladder or a volumetric change of the bladder as a result of forces acting on the bladder, and wherein the second parameter comprises the amount of fluid displaced from the bladder, the volumetric change of the bladder, or the change of pressure within the bladder caused by the tremor, and wherein the processor is operatively coupled to the second sensing module and configured to:

perform an analysis of the fluid displaced from the bladder, the volumetric change of the bladder, or the change of pressure within the bladder, and based on the analysis determine whether the tremor has a frequency in the at least one predetermined frequency range that is indicative of OSA.

13. The apparatus according to claim 1, further comprising:

a second sensing module configured to measure a second parameter indicative of the tremor in the patient's neck, tongue and/or throat muscles while the patient s awake, the second parameter not being airflow through the patient's airway, wherein the second sensing module comprises a pharyngometer configured to propagate sound pulses into the patient's airway and detect reflection waves generated in response to the sound pulses, wherein the second parameter comprises the reflection waves, and wherein the processor is operatively coupled to the second sensing module and configured to:

perform an analysis of the reflection waves by generating a plurality of patient airway dimensional measurements, and based on the analysis determine whether the airway dimensional measurements are indicative of OSA.

14. The apparatus according to claim 1, further comprising:

a second sensing module structured to measure a second parameter indicative of the tremor in the patient's neck, tongue and/or throat muscles while the patient is awake, the second parameter not being airflow through the patient's airway, wherein the second sensing module comprises one or more stimulation electrodes and one or more sensing electrodes, the one or more stimulation electrodes being configured to stimulate a target nerve or a nerve which innervates the target nerve, the target nerve being associated with the patient's neck, tongue and/or throat muscles, wherein the second parameter comprises a one or more target nerve signals collected by the one or more sensing electrodes, the one or more target nerve signals being modulated by the tremor, and wherein the processor is operatively coupled to the second sensing module and configured to:

perform an analysis of one or more target nerve signals, and based on the analysis determine whether the tremor has a frequency in the at least one predetermined frequency range that is indicative of OSA.

15. An apparatus for use in determining whether a tremor in a patient's neck, tongue and/or throat muscles has a frequency in at least one predetermined frequency range that is indicative of obstructive sleep apnea (OSA) in the patient, comprising:

a first sensing module configured to measure a first parameter indicative of a tremor in the patient's neck, tongue and/or throat muscles while the patient is awake, the first sensing module generating one or more first electrical signals based on the measured first parameter while the patient is awake, wherein the first sensing module is further configured to measure velocity of a surface of the tongue and wherein the first parameter is velocity of the surface of the tongue caused by the tremor;

a second sensing module configured to measure a second parameter indicative of a tremor in the patient's neck, tongue and/or throat muscles while the patient is awake, the second parameter being different than the first parameter, the second sensing module generating one or more second electrical signals based on the measured second parameter while the patient is awake;

a processor operatively coupled to the first sensing module and the second sensing module, the processor being configured to:

(i) receive the one or more first electrical signals for a plurality of breathing cycles of the patient, select a subset of the plurality of breathing cycles that best fit a mean breathing cycle for the patient, wherein selecting the subset includes filtering the plurality of breaths based on a minimum length of the breathing cycles and selecting the breathing cycles having the minimum length, perform a first analysis of the one or more first electrical signals from the subset, and based on the first analysis make a first determination as to whether the tremor has a frequency in at least one predetermined frequency range that is indicative of OSA, the at least one predetermined frequency range being associated with and characteristic of an increased compensatory muscular activation of the upper airway of the patient during wakefulness, (ii) receive the one or more second electrical signals for the plurality of breathing cycles of the patient, perform a second analysis of the one or more second electrical signals from the selected subset of the plurality of breathing cycles, and based on the second analysis make a second determination as to whether the tremor has a frequency in the at least one predetermined frequency range that is indicative of OSA, and (iii) determine whether the patient has OSA based on at least the first determination and the second determination.

16. The apparatus according to claim 15, wherein the processor is configured to determine whether the tremor is indicative of OSA only if both the first determination and the second determination determines that the tremor has a frequency in the at least one predetermined frequency range.

17. The apparatus according to claim 16, wherein the at least one predetermined frequency range is below 100 Hz.

18. The apparatus according to claim 17, wherein the at least one predetermined frequency range is 30-40 Hz.

19. The apparatus according to claim 15, further comprising a third sensing module configured to measure a third parameter indicative of a tremor in the patient's neck, tongue and/or throat muscles while the patient is awake, the third parameter being different than the first parameter and the second parameter, the third sensing module generating one or more third electrical signals based on the measured third parameter, the processor being structured to receive the one or more third electrical signals for the plurality of breathing cycles, perform a third analysis of the one or more third electrical signals from the subset of breathing cycles, and based on the third analysis make a third determination as to whether the tremor has a frequency in the at least one predetermined frequency range that is indicative of OSA, and wherein the processor is structured to determine whether the tremor is indicative of OSA based on at least the first determination, the second determination and the third determination.

20. The apparatus according to claim 19, wherein the processor is configured to determine that the tremor is indicative of OSA if at least two of the first determination, the second determination and the third determination determines that the tremor has a frequency in the at least one predetermined frequency range.

21. The apparatus according to claim 19, wherein the processor is configured to determine that the tremor is indicative of OSA only if each of the first determination, the second determination and the third determination determines that the tremor has a frequency in the at least one predetermined frequency range.

* * * * *